United States Patent [19]
Kurys et al.

[11] Patent Number: 6,004,977
[45] Date of Patent: Dec. 21, 1999

[54] N-(PYRIDINYLAMINO) ISOINDOLINES AND RELATED COMPOUNDS

[75] Inventors: Barbara E. Kurys, Long Valley; David M. Fink, Lebanon; Brian S. Freed; Gregory H. Merriman, both of Phillipsburg, all of N.J.

[73] Assignee: Hoechst Marion Roussel, Inc., Bridgewater, N.J.

[21] Appl. No.: 08/959,789

[22] Filed: Oct. 29, 1997

Related U.S. Application Data

[60] Provisional application No. 60/060,948, Dec. 27, 1996.

[51] Int. Cl.⁶ .......................... A01N 43/42; A01N 43/40; C07C 211/00; C07D 401/00
[52] U.S. Cl. .............................. 514/307; 514/1; 514/183; 514/277; 514/279; 514/315; 514/352; 564/305; 546/272; 546/277.1; 536/22.1; 536/23.1
[58] Field of Search ................................ 514/1, 187, 277, 514/279, 307, 315, 352; 564/305; 546/272, 277.1; 536/22.1, 23.1

[56] References Cited

U.S. PATENT DOCUMENTS

| | | | |
|---|---|---|---|
| 4,124,375 | 11/1978 | Bollinger et al. | 71/96 |
| 4,210,749 | 7/1980 | Shetty | 542/469 |
| 5,102,891 | 4/1992 | Effland et al. | 514/307 |
| 5,567,718 | 10/1996 | Shutske et al. | 514/339 |

OTHER PUBLICATIONS

R.D. Clark, et al., J. Med. Chem., 33, 596–600 (1990).
Hussein, et al., Asian J. of Chem., vol. 3, No. 1 pp. 30–37 (1991).
Truitt et al., New Compounds vol. 8, pp. 731–732 (1965).
Suzuki, et al., J. Heterocyclic Chem. 16, pp. 645–648 (1979).
Organic Syntheses, pp. 1065–1066, vol. 5, 1973.
Organic Syntheses, pp. 406–407, vol. 5, 1973.
Gschwend et al., "Synthetic Approaches to 9–Chloro–7–(o–fluorophenyl)–5H–dibenz[c,e]azepine," J. Org. Chem. 1982, 47, 3652–3657.

*Primary Examiner*—Jezia Riley
*Attorney, Agent, or Firm*—Balaram Gupta

[57] ABSTRACT

Novel N-(pyridinylamino)isoindolines and related compounds, intermediates and processes for the preparation thereof, and methods of relieving memory dysfunction and treating depression utilizing the N-(pyridinylamino) isoindolines and related compounds, the intermediates or compositions thereof are disclosed.

17 Claims, No Drawings

N-(PYRIDINYLAMINO) ISOINDOLINES AND RELATED COMPOUNDS

This application claims the benefit of U.S. Provisional Application Ser. No. 60/060,948, filed Dec. 27, 1996.

SUMMARY OF THE INVENTION

The present invention relates to N-(pyridinylamino) isoindolines and related compounds. More particularly, the present invention relates to N-(pyridinylamino)isoindolines and related compounds of formula 1

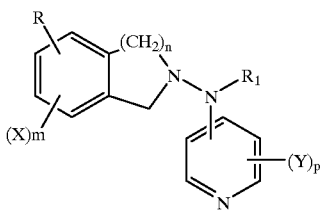

1 wherein R is hydrogen, a group of the formula $R_2O$— wherein $R_2$ is hydrogen, loweralkyl, benzyl, a group of the formula $(R_3)_3Si$— wherein $R_3$ is loweralkyl, or a group of the formula $R_4R_5NCO$— wherein $R_4$ and $R_5$ are independently hydrogen, loweralkyl or benzyl; $R_4$ and $R_5$ taken together with the nitrogen atom to which they are attached form a group of the formula

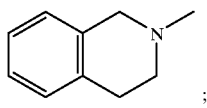

;

or a group of the formula

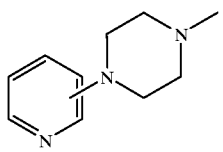

$R_1$ is hydrogen or loweralkyl; X is hydrogen, loweralkyl, halogen, hydroxy, loweralkoxy or trifluoromethyl; Y is hydrogen, loweralkyl, halogen, hydroxy, loweralkoxy or trifluoromethyl; m is 1 or 2; n is 1, 2, or 3; p is 1 or 2; the optical isomers thereof; or the pharmaceutically acceptable salts thereof, which are useful in relieving memory dysfunction and thus indicated in the treatment of Alzheimer's disease, as well as useful in the treatment of depression.

Preferred N-(pyridinylamino)isoindolines and related compounds are those wherein R is a group of the formula $R_2O$— wherein $R_2$ is a group of the formula $R_4R_5NCO$ wherein $R_4$ and $R_5$ are as hereindescribed.

The present invention also relates to N-(pyridinylamino)phthalimides of formula 2

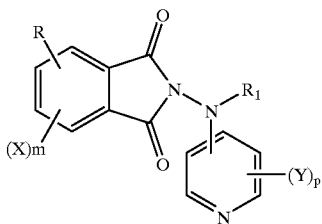

2 wherein R is $R_2O$— wherein $R_2$ is hydrogen or loweralkyl; $R_1$ is hydrogen or loweralkyl; X is hydrogen, loweralkyl, halogen, hydroxy, loweralkoxy or trifluoromethyl; Y is hydrogen, loweralkyl, halogen, hydroxy, loweralkoxy or trifluoromethyl; m and p are 1 or 2; the pharmaceutically acceptable salts thereof or the optical isomers thereof, N-(pyridinylamino)hydrazones of formula 3

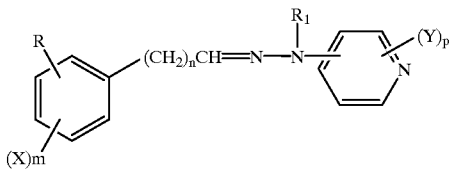

3 wherein R is hydrogen, a group of the formula $R_2O$— wherein $R_2$ is hydrogen, loweralkyl, benzyl or a group of the formula $(R_3)_3Si$— wherein $R_3$ is loweralkyl; X is hydrogen, loweralkyl, hydroxy, loweralkoxy, halogen or trifluoromethyl; Y is hydrogen, loweralkyl, hydroxy, loweralkoxy, halogen or trifluoromethyl; n is 1, 2 or 3; or the optical isomers thereof, and N-(pyridinylamino)hydrazines of formula 4

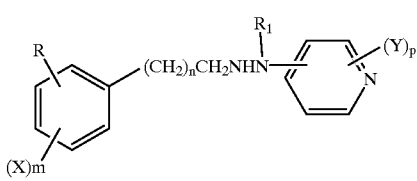

4 wherein R is hydrogen, a group of the formula $R_2O$— wherein $R_2$ is hydrogen, loweralkyl, benzyl or a group of the formula $(R_3)_3Si$— wherein $R_3$ is loweralkyl; X is hydrogen, loweralkyl, hydroxy, loweralkoxy, halogen or trifluoromethyl; Y is hydrogen, loweralkyl, hydroxy, loweralkoxy, halogen or trifluoromethyl; n is 1, 2 or 3; or the optical isomers thereof, which are useful as intermediates for the preparation of the present N-(pyridinylamino)isoindolines and related compounds.

In addition, the present invention relates to isoquinolindiones of formula 14

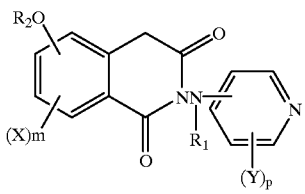

14 wherein $R_2$ is hydrogen or loweralkyl; $R_1$ is hydrogen or loweralkyl; X is hydrogen, loweralkyl, halogen, hydroxy, loweralkoxy or trifluoromethyl; Y is hydrogen, loweralkyl, halogen, hydroxy, loweralkoxy or trifluoromethyl; m and p are 1 or 2; or the optical isomers thereof, also useful for the synthesis of the N-(pyridinylamino)isoquinolines of the present invention and compounds related thereto.

DETAILED DESCRIPTION OF THE INVENTION

As used throughout the specification and appended claims, the term "alkyl" refers to a straight or branched chain hydrocarbon radical containing no saturation and having 1 to 8 carbon atoms. Examples of alkyl groups are methyl, ethyl, 1-propyl, 2-propyl, 1-butyl, 1-hexyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The term "alkanoic acid" refers to a compound formed by combination of a carboxyl group with a hydrogen atom or alkyl group. Examples of alkanoic acid are formic acid, acetic acid, propanoic acid, 2,2-dimethylpropanoic acid, hexanoic acid, octanoic acid and the like. The term "halogen" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes arid as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel N-(pyridinylamino)isoindolines and related compounds of the present invention are prepared by the processes delineated in Reaction Schemes, the tetrahydroisoquinolines and tetrahydroazepines shown therein, being the related compounds.

Entry into the N-(pyridinylamino)isoindoline series, that is, the series of compounds of formula 1, wherein n is 1, is gained by the sequence of reactions delineated in Reaction Scheme A. Condensation of a phthalic anhydride 5, which is commercially available or readily preparable, with an N-(pyridinyl)hydrazine of formula 6, affords an N-(pyridinyl)phthalimide 7 which is reduced to an N-(pyridinyl)isoindoline 8. The condensation is generally performed using a hydrohalide salt of the hydrazine 6, such as the hydrochloride salt, in an alkanoic acid, such as acetic acid, at the reflux temperature of the reaction medium, although reduced reaction temperatures may be employed.

The reduction of phthalimide 7 is accomplished by means of an alkali metal aluminum hydride in an ethereal solvent. Among alkali metal aluminum hydrides, there may be mentioned lithium aluminum hydride, sodium aluminum hydride and potassium aluminum hydride. Among ethereal solvents there may be mentioned diethyl ether, 1,2-dimethyoxyethane, methyl tert-butyl ether, 2-methoxyethyl ether, dioxane and tetrahydrofuran. Lithium aluminum hydride and tetrahydrofuran is the preferred reaction medium. The reduction temperature is not narrowly critical. While it is preferred to conduct the reduction at ambient temperature, the reduction may be conducted at either an elevated or reduced temperature consistent with the reaction medium.

The conversion of phthalic anhydride 5 to isoindoline 8 may be carried out without characterization of the intermediate phthalimide 7 in essentially a one-pot reaction. For example, the condensation of a phthalic anhydride 5 with a hydrazine 6 may be conducted in acetic acid, and after the reaction is determined to be complete, the acetic acid is removed, the residue is triturated with an alkanol, such as 2-propanol, and the crude phthalimide 6 is reduced with lithium aluminum hydride in tetrahydrofuran.

Alternatively, entry into the N-(pyridinylamino)isoindoline series of compounds of formula 1 wherein n is 1 may be achieved by condensing a 1,2-dihalomethylbenzene 9 wherein Hal is chloro or bromo with a hydrazine 6 in a dipolar aprotic solvent, for example, dimethylacetamide, dimethylformamide, hexamethylphosphoramide, or dimethylsulfoxide in the presence of an acid acceptor, for example, pyridine, 4-dimethylaminopyridine, triethylamine or tripropylamine, at about ambient temperatures, although reduced or elevated temperatures may be employed depending upon the selected reaction medium. Dimethylformamide is the preferred solvent; triethyl amine is the preferred acid acceptor.

To prepare a carbamoyloxy-N-(pyridinylamino)isoindoline 11 wherein $R_4$ and $R_5$ are as hereinmentioned, that is, to introduce the

moiety into the indoline, a hydroxy-N-(pyridinylamino)isoindoline 10 is treated with an isocyanate of formula 12

$$R_4N=C=O \qquad 12$$

wherein $R_4$ is loweralkyl in a suitable solvent such as acetonitrile in the presence of a catalytic amount of mild base, such as 1,8-diazabicyclo[5.4.0]undec-7-ene, at ambient temperature (although elevated temperatures may be employed) conditions providing the desired carbamate 11 wherein $R_4$ is loweralkyl and $R_5$ is hydrogen. Treatment of a phenol 10 with a carbamoyl halide 13A $$R_4R_5NCOHal \qquad 13A$$

wherein $R_4$, $R_5$ and Hal are as hereindescribed in a suitable solvent such as a halocarbon (e.g., dichloromethane, trichloromethane, or 1,1- or 1,2-dichloroethane) in the presence of an acid acceptor such as trialkylamine (e.g., triethylamine or 4-dimethylaminopyridine) at the reflux temperature of the reaction medium (although reduced temperatures may be employed), also provides the desired carbamate 11, in this case, wherein $R_4$ and $R_5$ are loweralkyl.

In the event an N-(pyridinylamine)isoindoline 8 does not bear a phenolic hydroxyl group, that is, $R_2$ is not hydrogen, the group $R_2O$— must be cleaved prior to introduction of an aminocarbonyl ($R_4R_5NCO$) function. When $R_2$ is loweralkyl, the cleavage is effected by a hydrohalic acid, for example, hydrobromic acid at the reflux temperature of the reaction medium. Alternatively, the cleavage is effected by means of a boron trihalide such as boron tribromide in a halocarbon such as dichloromethane at ambient temperature. In the same vein, when $R_2$ is a group of the formula $(R_3)_3Si$—, the moiety $R_2O$— must be cleaved prior to formation of the carbamoyloxy function. The cleavage, in this case, is effected by tetra-n-butyl ammonium fluoride in an ethereal solvent, e.g., tetrahydrofuran at ambient temperature.

To gain entry into the N-(pyridinylamino)isoquinoline series, that is, the series of compounds where n is 2, a homophthalic anhydride 13 is condensed with a hydrazine 6 to provide an isoquinolinedione 14 which is reduced to an isoquinoline 15. The condensation and reduction are performed as described herein for the analogous processes in the isoindoline series, as are the cleavage and carbamylation reactions to provide phenol 18 and carbamate 19, respectively, as shown in reaction Scheme B.

Also, in a manner analogous to processes shown in Reaction Scheme A for conversion of a dihalomethylbenzene 9 to isoindoline 8 with hydrazine 6, a haloethylhalomethylbenzene 17 is converted to a tetrahydroisoquinoline 15 by hydrazine 6. Alternatively, entry into the N-(pyridinylamino)isoquinoline series is achieved by cyclizing a hydrazinoethylbenzene 16 with a halomethylalkyl ether of formula 20.

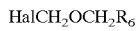

wherein $R_6$ is loweralkyl in an alkanoic acid such as, for example, acetic acid at about 55° C. to the reflux temperature of the reaction medium.

The hydrazinoethylbenzene 16 is prepared from phenylacetaldehyde 28, or the enol ether 29 thereof, by condensation with hydrazine 6 followed by reduction of the resulting hydrazone 30 by the processes described below for the synthesis of hydrazinopropylbenzene 23 (Scheme C).

In the event the phenolic hydroxyl group of a tetrahydroisoquinoline 15 is protected as a benzyloxy function, that is, is in the form of a group $R_2O$ wherein $R_2$ is benzyl, the protected tetrahydroisoquinoline is debenzylated to phenol 18 by hydrogenation over, for example, a noble metal catalyst, such as palladium, preferably supported on carbon, at a pressure of about 55 psig in an alkanol such as methanol. In the event the hydroxyl group is present as an alkoxy function, the alkoxy function is cleaved by a boron trihalide as in the isoindoline series.

To gain access to the N-(pyridinylamino)azepinyl series, that is, the series of compounds of formula 1 wherein n is 2, a phenylpropionyl aldehyde 21 is condensed with a pyridinylhydrazine 6 to form a pyridinylhydrazone 22 which is reduced to a pyridinylhydrazine 23 and then cyclized with a halomethylalkylether 20 to a pyridinylaminoazepine 24. The condensation of an aldehyde 21 with a hydrazine 6 is effected in an alkanol, for example, methanol, ethanol, or 1- or 2- propanol, ethanol being preferred, in the presence of a drying agent to remove the formed water, for example, anhydrous magnesium sulfate at the reflux temperature of the reaction medium. The condensation temperature is not narrowly critical and a reaction temperature from ambient to reflux may be employed.

The condensation of an aldehyde 21 with a hydrazine 6 to provide hydrazone 22 may be carried out with an enol ether 27 wherein $R_7$ is loweralkyl, the equivalent of an aldehyde 21. In this aspect, the condensation is accomplished in an alkanol such as methanol, ethanol, 1-, or 2-propanol in the presence of an organic acid such as methanesulfonic acid, benzenesulfonic acid or 4-methylbenzenesulfonic acid, conveniently at the reflux temperature of the condensation medium. Ethanol is the preferred alkanol; 4-methylbenzenesulfonic acid is the preferred organic acid. Reaction temperatures from ambient to the reflux temperature may be employed.

The reduction of hydrazone 22 to hydrazine 23 is conducted in an ethereal solvent utilizing an alkali metal aluminum hydride as the reducing agent. Among ethereal solvents are diethylether, 1,2-dimethoxyether, 2-methoxyethyl ether, dioxane or tetrahydrofuran. Among alkali metal aluminum hydride reducing agents are lithium aluminum hydride, sodium aluminum hydride, or potassium aluminum hydride. Lithium aluminum hydride and tetrahydrofuran are the preferred solvent and reducing agent. Ambient temperature is the preferred reduction temperature; the reduction may be performed at reduced or elevated temperatures, however.

The cyclization of a hydrazine 23 with a halomethylalkyl ether 20 is conducted as described herein.

The cleavage, if necessary, of the $R_2O$-moiety of 24 to a phenol 25 and the carbamylation of phenol 25 to a carbamate 26 are also conducted as hereindescribed.

As hereinbefore mentioned, the requisite starting materials for the preparation of the N-(pyridinylamino)isoindolines and related compounds of the present invention are either commercially available or preparable by processes described in the literature mentioned herein. As reported by P. A. Harland and P. Hodge in Synthesis, 223 (1982), condensation of cyclohexa-1, 3-dienes with dialkyl acetylene dicarboxylates followed by elimination of ethylene provides phthalates, which may be hydrolyzed and cyclized by conventional methods to phthalic anhydrides. Phthalic anhydrides are also prepared by oxidation of 1,2-dimethylbenzenes to 1,2-benzenedicarboxylic acids and dehydration to the anhydrides, as reported by B. V. Shelty in U.S. Pat. No. 4,210,749 issued Jul. 1, 1980. Phthalic anhydrides are also prepared via oxazolines as described herein.

The requisite 2-halomethylbenzyl halides, starting materials for the synthesis of the N-(pyridinylamino)isoindolines, are available from phthalic anhydrides by the processes disclosed by B. V. Shelty in U.S. Pat. No. 4,210,749, as well as those described herein.

Homophthalic acids, the starting material for the preparation of the related N-(pyridinylamino)tetrahydroisoquinolines, are available from benzoic acids by conventional processes as described by H. K. Desai and R. N. Usgaonkar in the Journal of the Indian Chemical Society, 40, 239 (1963) and S. P. Inamdar and R. N. Usgaonkar in the Journal of the Indian Chemical Society, 43, 615 (1966).

2-(Haloethyl)benzyl halides, required for the preparation of the N-(pyridinylamino)tetrahydroisoquinolines of the present invention, are accessible by cleavage of isochromans with hydrohalic acids as described herein.

The phenylacetaldehyde and phenylpropionylaldehyde starting materials are prepared from phenylacetic acids or phenylpropionic acids, or the esters thereof, by reduction to the corresponding carbinols and oxidation thereof to the desired aldehydes, as described herein and by methods reported by M. Elliott, et al., Pesticide Science, 18, 223 (1987).

The enol ether starting materials are prepared from the appropriate benzaldehyde by conventional methods utilizing methoxymethyltriphenylphosphonium chloride in the presence of a base as reported in Synthesis, 796 (1975).

The N-(pyridinylamino)isoindolines and related compounds of the present invention are useful as agents for the relief of memory dysfunction, particularly dysfunctions associated with decreased cholinergic activity such as those found in Alzheimer's disease. Relief of memory dysfunction activity is demonstrated in the in vitro inhibition of acetylcholinesterase assay, an assay for the determination of the ability of a drug to inhibit the inactivation of acetylcholine, a neurotransmitter implicated in the etiology of memory dysfunction and Alzheimer's dementia. In this assay, a modification of a lest described by G. L. Ellman, et al., Biochemical Pharmacology, 7, 88 (1961), the following reagents are prepared and employed:

1. 0.05 M Phosphate Buffer (pH 7.2)

A solution of monobasic sodium phosphate monohydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate in Buffer

The 0.05 m Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic acid in Buffer

The 0.05 m Phosphate Buffer (pH 7.2) was added to 5,5-dithiobisnitrobenzoic acid to a total volume of 100 ml, i.e., a quantity sufficient (gs) to 100 ml.

4. Stock Solution of Drug

A 2 millimolar stock: solution of the test drug is prepared in a quantity sufficient of either acetic acid or dimethyl sulfoxide to volume with 5,5-dithiobisnitrobenzoic acid in Buffer. Stock Solution of Drug is serially diluted (1:10) so that the final cuvette concentration is $10^{-4}$ molar.

Male Wistar rats are decapitated, brains rapidly removed, corpora striata dissected free, weighted and homogenized in 19 volumes (approximately 7 mg protein/ml) of 0.05 m Phosphate Buffer (pH 7.2) using a Potter-Elvejhem homogenizer. A 25 ml aliquot of this suspension is added to 1 ml of the vehicle or various concentrations of the test drug and preincubated for 10 minutes at 37° C. Enzyme activity is measured with a Beckman DU-50 spectrophotometer with the following software and instrument settings:

1. Kinetics Soft-PacÔ Module #598273;
2. Program #6 Kindata;
3. Source—Vis;
4. Wavelength—412 nm;
5. Sipper—none;
6. Cuvettes—2 ml cuvettes using auto 6-sampler;
7. Blank—1 for each substrate concentration;
8. Interval time—15 seconds (15 or 30 seconds for kinetics);
9. Total time—5 minutes (5 to 10 minutes for kinetics);
10. Plot—yes;
11. Span—autoscale;
12. Slope—increasing;
13. Results—yes (gives slope); and
14. Factor—1.

Reagents are added to the blank and sample cuvettes as follows:

1. Blank: 0.8 ml 5,5-Dithiobisnitrobenzoic Acid
   0.8 m Substrate in Buffer
2. Control: 0.8 ml 5,5-Dithiobisnitrobenzoic Acid/ Enzyme
   0.8 ml Substrate in Buffer
3. Drug: 0.8 ml 5,5-Dithiobisnitrobenzoic Acid/Drug/ Enzyme
   0.8 ml Substrate in Buffer Blank values are determined for each run to control for non-enzymatic hydrolysis of substrate and these values are automatically subtracted by the Kindata program available on kinetics soft-pac module. This program also calculates the rate of absorbance change for each cuvette.

For $IC_{50}$ Determinations

Substrate concentration is 10 millimolar diluted 1:2 in assay yielding final concentration of 5 millimolar. 5,5-dithiobisnitrobenzoic acid concentration is 0.5 millimolar yielding 0.25 millimolar final concentration.

$$\% \text{ Inhibition} = \frac{\text{Slope Control} - \text{Slope drug}}{\text{Slope Control}} \times 100$$

$IC_{50}$ values are calculated from log-probit analysis

TABLE I

| Compound | Inhibition of Acetylcholinesterase Activity $IC_{50}$(mM) |
|---|---|
| 2,3-dihydro-2-[(N-2-pyridinyl)amino]-1H-isoindol-5-yl methyl carbamate | 3.56 |
| 2,3-dihydro-2-[(N-2-pyridinyl)amino]-1H-isoindol-7-yl methyl carbamate | 0.174 |
| 2,3-dihydro-2-(-4-pyridinylamino)-1H-isoindol-4-yl dimethylcarbamate | 0.029 |
| 6-methoxy-2-(pyridin-4-yl-amino)-1,2,3,4-tetrahydro-isoquinolin-7-yl dimethyl carbamate | 0.076 |
| 2-(4-pyridinylamino)-1,2,3,4-tetrahydroisoquinolin-6-yl dimethyl carbamate | 12.71 |
| 2-(4-pyridinylamino)-1,2,3,4-tetrahydroisoquinolin-7-yl dimethyl carbamate | 0.56 |
| 7-methoxy-2-(4-pyridinylamino)-1,2,3,4-tetrahydro-isoquinolin-6-yl dimethyl carbamate | 1.4 |
| dimethyl-carbamic acid 2-((4-pyridinylamino)-2,3,4,5-tetrahydro-1H-benzo[c]azepin-7-yl ester | 0.34 |
| tacrine (reference) | 0.31 |

Relief of memory dysfunction is achieved when the present N-(pyridinylamino)isoindolines and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compounds. It is to be further understood that the dosages set forth herein are exemplary only and that they do not, to any extent, limit the scope or practice of the invention.

The N-(pyridinylamino)isoindolines and related compounds of the present invention are also useful as agents for treating depression. Depression treatment is demonstrated in the in vitro clonidine binding: $a_2$-receptor assay, an assay for the determination of the ability of a drug to bind the clonidine $a_2$-receptor, patterned after assays described by D. C. U'Prichard, et al., Molecular Pharmacology, 15, 47 (1979) and D. C. U'Prichard, et al., ibid, 13, 454, (1977).

The following reagents are prepared:
1. Tris buffer, pH 7.7
   a. 57.2 g Tris hydrochloric acid 16.2 g Tris Base—q.s. to 1 liter(0.5 M Tris buffer, pH 7.7)
   b. Make a 1:10 dilution in distilled $H_2O$ (0.05 M Tris buffer, ph 7.7)
2. Tris buffer containing physiological ions
   a. Stock Buffer Sodium chloride 7.014 g Potassium chloride 0.372 g Calcium chloride 0.222 g—q.s. to 100 ml in 0.5 Tris buffer Magnesium chloride 0.204 g
   b. Dilute 1:10 in distilled $H_2O$. This yields 0.05 M Tris hydrochloric acid, pH 7.7; containing sodium chloride (120 mM), potassium chloride (5 mM), calcium chloride (2 mM) and magnesium chloride (1 mM)
3. [4-$^3$H]-Clonidine hydrochloride (20–30 Ci/mmol) is obtained from New England Nuclear. For $IC_{50}$ determinations: $^3$H-clonidine is made up to a concentration of 120 nM and 50 ml of it is added to each tube (yields a final concentration of 3 nM in the 2 ml volume assay).
4. Clonidine hydrochloride is obtained from Boehringer Ingelheim. A stock solution of 0.1 mN clonidine is made up to determine nonspecific binding. This yields a final concentration of 1 mM in the assay (20 ml to 2 ml).
5. Test compounds. For most assays, a 1 mM stock solution is made up in a suitable solvent and serially diluted, such that the final concentration in the assay ranges from $10^{-5}$ to $10^{-8}$M. Seven concentrations are used for each assay an higher or lower concentrations may be used, depending on the potency of the drug.

B. Tissue Preparation

Male Wistar rats are sacrificed by decapitation and the cortical tissue rapidly dissected. The tissue is homogenized in 50 volumes of 0.05 M Tris buffer, pH 7.7 (buffer 1b) with the Brinkman Polytron, then centrifuged at 40,000 g for 15 minutes. The supernatant is discarded and the pellet rehomogenized in the original volume of 0 05 M Tris buffer, pH 7.7 and recentrifuged as before. The supernate is discarded and the final pellet rehomogenized in 50 volumes of Buffer 2b. This tissue suspension is then stored on ice. The final tissue concentration is 10 mg/ml. Specific binding is 1% of the total added ligand and 80% of total bound ligand.

C. Assay 100 ml 0.5 M Tris-physiological salts, pH 7.7 (buffer 2a)
830 ml $H_2O$
20 ml Vehicle (for total binding) or 0.1 mM clonidine (for nonspecific binding) or appropriate drug concentration
50 ml $^3$H-clonidine stock
1000 ml Tissue suspension Tissue homogenates are incubated for 20 minutes at 25° C. with 3 nM $^3$H-clonidine and varying drug concentrations, then immediately filtered under reduced pressure on Whatman GF/B filters. The filters are washed with three five ml volumes of ice-cold 0.05 M Tris buffer, pH 7.7, then transferred to scintillation vials. Ten ml of liquescent counting solution is added to each sample which is then counted by liquid scintillation spectroscopy. Specific clonidine is defined as the difference between total bound and that performed using log-probit analysis. The percent inhibition at each drug concentration is the mean of triplicate determinations.

TABLE II

| Compound | Inhibition of clonidine binding activity $IC_{50}$ (mM) |
|---|---|
| 2,3-dihydro-N-2-pyridinyl-1H-isoindol-2-amine | 7.58 |
| 2,3-dihydro-7-methoxy-N-2-pyridinyl-2H-isoindol-2-amine | 2.79 |
| 3,4-dihydro-N-4-pyridinyl-2(1H)-isoquinolinamine | 0.084 |
| 2,3-dihydro-N-4-pyridinyl-1H-isoindol-2-amine | 0.064 |
| 1,4-dihydro-2-[(N-4-pyndinyl)amino]-3(2H)-isoquinolinone | 3.88 |
| 2,3-dihydro-4-methoxy-N-(pyridinyl)-1H-isoindol-2-amine | 0.035 |
| 2,3-dihydro-N-methyl-N-(4-pyridinyl)-1H-isoindol-2-amine | 0.08 |
| 2,3-dihydro-2-(-4-pyridinylamino)-1H-isoindol-4-ol | 0.034 |
| 2,3-dihydro-2-(-4-pyridinylamino)-1H-isoindol-4-yl dimethylcarbamate | 3.82 |
| (7-methoxy-1,3,4,5-tetrahydro-2-benzo[c]azepinyl)-4-pyridinylamine | 2.67 |
| amitriptyline (reference) | 0.039 |

Depression treatment is achieved when the present N-(pyridinylamino)isoindolines and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Acetylcholinesterase inhibitors and clonidine binding inhibitors are known in the art as being useful as relievers of memory dysfunction and as antidepressants, respectively. (See V. Kumar in Alzheimer's Disease: Therapeutic Strategies, E. Giacobini and R. Becker Eds.; Birkhauser, Boston 1994, for memory dysfunction relief utility and K. F. Tipton in Biochemical and Pharmacological Aspects of Depression, K. F. Tipton and U. B. H. Youdin, Eds., Taylor and Francis, London 1989, for antidepressant utility).

Depression frequently attends memory dysfunction associated with Alzheimer's disease and responds to antidepressant intervention. Thus, the antidepressant component of the pharmacological properties of the compounds of the present invention provide both desirable effects in one chemical entity, providing both therapies in one administration, where indicated. See, for example, W. W. Pendlebury and P. R. Solomon, Neurobiology of Aging, 15, 287 (1994) at page 287, among others.

Effective amounts of the compounds of the invention may be administered to a subject by any one of various methods, for example orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, arid salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mg of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or thyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple vials made of glass or plastic.

Compounds of the present invention include:
a. 2,3-dihydro-4-methyl-N-4-pyridinyl-1H-isoindol-2-amine;
b. 2,3-dihydro-N-4-pyridinyl-4-trifluoromethyl-1H-isoindol-2-amine;
c. (3,4-dihydro-8-methoxy-1H-isoquinolin-2-yl)-4-(3-methylpyridinyl)amine;
d. (3,4-dihydro-8-methoxy-1H-isoquinolin-2-yl)-4-(3-methoxypyridinyl)amine;
e. (3,4-dihydro-8-methoxy-1H-isoquinolin-2-yl)-4-(3-hydroxypyridinyl)amine;
f. (3,4-dihydro-8-methoxy-1H-isoquinolin-2-yl)-4-(3-bromopyridinyl)amine;
g. (3,4-dihydro-8-methoxy-1H-isoquinolin-2-yl)-4-(3-trifluoromethyl)amine;
h. 2,3-dihydro-7-methoxy-N-2-(4-methylpyridinyl)-2H-isoindol-2-amine;
i. 2,3-dihydro-7-methoxy-N-2-(4-methoxypyridinyl)-2H-isoindol-2-amine;
j. 2,3-dihydro-7-methoxy-N-2-(4-hydroxypyridinyl)-2H-isoindol-2-amine;
k. 2,3-dihydro-7-methoxy-N-2-(4-chloropyridinyl)-2H-isoindol-2-amine;
l. 2,3-dihydro-7-methoxy-N-2-(4-trifluoromethylpyridinyl)-2H-isoindol-2-amine;
m. N-[3-(3-methylphenyl)propylidine]-N'-(4-pyridinyl)hydrazine;
n. N-[3-(3-hydroxyphenyl)propylidine]-N'-(4-pyridinyl)hydrazine;
o. N-[3-(3-trifluoromethyl)propylidine]-N'-(4-pyridinyl)hydrazine;
p. N-[2-(4-methylphenyl)ethyl]-N'-pyridin-4-yl hydrazine;
q. N-[2-(4-hydroxyphenyl)ethyl]-N'-pyridin-4-yl hydrazine;
r. N-[2-(4-trifluoromethyl)ethyl-N'-pyridin-4-yl hydrazine;
s. 7-methyl-2-(4-pyridinylamino)-4H-isoquinoline-1,3-dione;
t. 7-chloro-2-(4-pyridinylamino)-4H-isoquinoline-1,3-dione;
u. 7-hydroxy-2-(4-pyridinylamino)-4H-isoquinoline-1,3-dione;
v. 7-trifluoromethyl-2-(4-pyridinylamino)-4H-isoquinoline-1,3-dione;
w. 7-methoxy-2-(2-methylpyridinyl-4-amino)-4H-isoquinoline-1,3-dione;
x. 7-methoxy-2-(2-bromopyridinyl-4-amino)-4H-isoquinoline-1,3-dione;
y. 7-methoxy-2-(3-hydroxypyridinyl-4-amino)-4H-isoquinoline-1,3-dione;
z. 7-methoxy-2-(3-methylpyridinyl-4-amino)-4H-isoquinoline-1,3-dione;
a'. 7-methoxy-2-(3-methoxypyridinyl-4-amino)-4H-isoquinoline-1,3-dione;
b'. 7-methoxy-2-(3-trifluoromethyl-4-pyridinyl)-4H-isoquinoline-1,3-dione.

The following examples are for illustrative purposes only and are not to be construed as limiting the invention in any way whatsoever. The reagents and starting materials are readily available to one of ordinary skill in the art. As used herein, the following terms have the indicated meanings: "kg" refers to kilograms; "g" refers to grams; "mg" refers to milligrams; "μg" refers to micrograms; "mmol" refers to millimoles; "L" refers to liters; "mL" refers to milliliters; "μL" refers to microliters; "cm" refers to centimeters; "M" refers to molar; "mM" refers to millimolar; "μM" refers to micromolar; "nM" refers to nanomolar; "eq" refers to equivalents; "N" refers to normal; "ppm" refers to parts per million; "δ" refers to parts per million down field from tetramethylsilane; "°C." refers to degrees Celsius; "°F." refers to degrees Fahrenheit; "mm Hg" refers to millimeters of mercury; "kPa" refers to kilopascals; "psi" refers to pounds per square inch; "rpm" refers to revolutions per minute; "bp" refers to boiling point; "mp" refers to melting point; "dec" refers to decomposition; "HPLC" refers to high performance liquid chromatography; "h" refers to hours; "min" refers to minutes; "sec" refers to seconds; "EtOAc" refers to ethyl acetate; "DCM" refers to dichloromethane; "THF" refers to tetrahydrofuran; "DMF" refers to N,N-dimethylformamide; "DMSO" refers to dimethyl sulfoxide; "LAH" refers to lithium aluminum hydride; "$R_f$" refers to retention factor; and "$R_t$" refers to retention time.

EXAMPLE 1

2,3-Dihydro-2-[(N-2-pyridinyl)amino]-1H-isoindol-5-yl methyl carbamate 2,3-Dihydro-2-[(N-2-pyridinyl)amino]-1H-isoindol-5-ol (0.8 g) was suspended in acetonitrile (50 ml) and 1,8-diazabicyclo[5.4.0]undec-7-ene (2 drops) was added, followed by methyl isocyanate (0.21 ml). The reaction mixture was stirred for about 15 mins and diluted with water and ethyl acetate. The organic layer was separated, washed with water and brine, dried over anhydrous sodium sulfate, filtered, and the filtrate was concentrated. The residue was chromatographed on silica gel using 50% methanol/ethyl acetate as the eluent. The appropriate fractions were collected to yield 0.6 g (60%) of product. Recrystallization of the product from ethyl acetate gave the analytical sample, mp 152–153° C.

Analysis: Calculated for $C_{15}H_{16}N_4O_2$: 63.37% C 5.67% H 19.71 % N Found: 63.36% C 5.58% H 19.66% N

EXAMPLE 2

2,3-Dihydro-5-[[tris(1-methylethyl)silyl]oxy]-N-2-pyridinyl-1H-isoindol-2-amine Triethylamine (10.9 ml) was added to a solution of 1,2-dibromomethyl-4-[[tri(1-methylethyl)silyl]oxy]benzene (17 g) and 2-hydrazinopyridine (4.3 g) in dimethylformamide (300 ml), and the reaction mixture was stirred, under nitrogen, at ambient temperature for about 20 mins and then diluted with water and ethyl acetate. The organic layer was separated, washed with water and brine, dried over anhydrous sodium sulfate, filtered, and the filtrate was concentrated. The residue was triturated with ethyl acetate to yield 5.7 g (38%) of product. Recrystallization of the product from ethyl acetate gave the analytical sample mp 95–96° C.

Analysis: Calculated for $C_{22}H_{33}N_3OSi$: 68.88% C 8.67% H 10.95% N Found: 68.65% C 8.79% H 10.89% N

EXAMPLE 3

2,3-Dihydro-N-2-pyridinyl-1H-isoindol-2-amine

Triethylamine (10.5 ml) was added to a solution of alpha,alpha'-dibromo-o-xylene (10 g) and 2-hydrazinopyridine (4.1 g) in dimethylformamide. The mixture was stirred, under nitrogen, at ambient temperature for about 20 mins and diluted with water and ethyl acetate. The organic layer was separated, washed with water and brine, dried over anhydrous sodium sulfate, filtered, and the filtrate was concentrated. Trituration of the residue with ethyl acetate gave 3.8 g (48%) of product. Recrystallization of the product from ethyl acetate afforded the analytical sample, mp 130–131° C.

Analysis: Calculated for $C_{13}H_{13}N_3$: 73.91 % C 6.20% H 19.89% N Found: 73.86% C 6.16% H 20.01% N

EXAMPLE 4

3,4-Dihydro-N-2-pyridinyl-2-(1H)-isoquinolinamine

Triethylamine (10.0 ml) was added to a solution of 1-bromomethyl-2-(2-bromoethyl)benzene (10 g) and 2-hydrazinopyridine (3.9 g) in dimethylformamide (250 ml), and the mixture was stirred, under nitrogen, at ambient temperature for about 20 mins. The reaction mixture was diluted with water and ethyl acetate. The organic layer was separated, washed with water and brine, dried over anhydrous sodium sulfate, filtered, and the filtrate was concentrated. The residue was triturated with ethyl acetate to afford 5.3 g (65%) of product. Recrystallization of the product from ethyl acetate gave the analytical sample, mp 116–117° C.

Analysis: Calculated for $C_{14}H_{15}N_3$: 74.64% C 6.71% H 18.65% N Found: 74.36% C 6.57% H 18.65% N

EXAMPLE 5

2,3-Dihydro-2-[(N-2-pyridinyl)amino]-1H-isoindol-5-ol hydrochloride

Tetrabutylammonium fluoride (13.0 ml) was added to a solution of 1,3-dihydro-5-[[tris)1-methylethyl)silyl]oxy]-N-2-pyridinyl-2H-isoindol-2-amine (5 g) in tetrahydrofuran (250 ml), and the mixture was stirred, under nitrogen, at ambient temperature for about 15 mins. The reaction mixture was diluted with water and ethyl acetate and the organic layer was separated, washed with water and brine, dried over anhydrous sodium sulfate, filtered, and the filtrate was concentrated. Trituration of the residue with ethyl acetate gave 1.8 g (61%) of product free base. The free base was dissolved in methanol and methanolic hydrogen chloride was added. The precipitate was collected and recrystallized from methanol/2-propanol to afford 0.40 g (14%) of product, mp>250° C.

Analysis: Calculated for $C_{13}H_{14}ClN_3O$: 59.21% C 5.35% H 15.93% N Found: 58.65% C 5.45% H 15.63% N

EXAMPLE 6

2,3-Dihydro-4-methoxy-N-2-pyridinyl-1H-isoindol-2-amine

Triethylamine (18.6 ml) was added to a solution of 1,2-dibromomethyl-3-methoxybenzene (19.6 g) and 2-hydrazinopyridine (7.27 g) in dimethylformamide (300 ml), and the mixture was stirred, under nitrogen, at ambient temperature for about 20 mins. The reaction mixture was diluted with water and ethyl acetate. The organic layer was separated, washed with water and brine, dried over anhydrous sodium sulfate, filtered, and the filtrate was concentrated. The residue was chromatographed on silica, eluting with 5% methanol/ethyl acetate. The appropriate fractions were collected and concentrated to yield 3.2 g (20%) of product. Trituration with ethyl acetate gave the analytical sample, mp 123–124° C.

Analysis: Calculated for $C_{14}H_{15}N_3O$: 69.69% C 6.27% H 17.41% N Found: 69.50% C 6.29% H 17.66% N

EXAMPLE 7

2,3-Dihydro-2-[(N-2-pyridinyl)amino]-1H-isoindol-4-ol hydrochloride 2,3-Dihydro-7-methoxy-N-2-pyridinyl-2H-isoindol-2-amine (3.2 g) in dichloromethane (25 ml) was added dropwise to a solution of boron tribromide (5.0 g) in dichloromethane (50 ml), and the mixture was stirred for 1 hr. The reaction mixture was quenched with water, basified with aqueous sodium bicarbonate solution, and extracted with 2-propanol/chloroform. The organic extracts were dried over anhydrous sodium sulfate, filtered, and the filtrate was concentrated. The residue was triturated with 2-propanol to give 1.8 g (60%) of product free base. The free base was dissolved in methanol and acidified with methanolic hydrogen chloride. The precipitate was recrystallized from hot methanol to afford (0.53 g) of product, mp 241–243° C.

Analysis: Calculated for $C_{13}H_{14}ClN_3O$: 59.21% C 5.35% H 15.93% N Found: 59.16% C 5.18% H 15.67% N

EXAMPLE 8

2,3-Dihydro-2-[(N-2-pyridinyl)amino]-1H-isoindol-4-yl methyl carbamate 2,3-Dihydro-2-[N-2-pyridinyl)amino]-1H-isoindol-4-ol (0.9 g) was suspended in acetonitrile (50 ml) and 1,8-diazabicyclo[5.4.0]undec-7-ene (2 drops) was added, followed by methyl isocyanate (0.23 ml). The reaction mixture was stirred for about 15 mins and diluted with water and ethyl acetate. The organic layer was separated and washed with water and brine, dried over anhydrous sodium sulfate, filtered, and the filtrate was concentrated. The residue was chromatographed on silica, eluting with 5% methanol/ethyl acetate. The appropriate fractions were collected and evaporated to yield 0.8 g (71%) of product. Recrystallization from chloroform gave the analytical sample, mp 200–201° C.

Analysis: Calculated for $C_{15}H_{16}N_4O_2$: 63.37% C 5.67% H 19.71% N Found: 63.19% C 5.59% H 19.48% N

EXAMPLE 9

3,4-Dihydro-N-4-pyridinyl-2-(1H)-isoquinolinamine

Homophthalic anhydride (5 g) and 4-hydrazinopyridine hydrochloride (4.5 g) were suspended in glacial acetic acid (300 ml), and the mixture was heated under reflux for 8 hrs. The reaction mixture was evaporated, and the residue was triturated with 2-propanol. The solid was collected by filtration and was dried to give 6.5 g of 2-[(N-4-pyridinyl)amino]-1,3-(2H 4H)isoindolindione hydrochloride. 1M lithium aluminum hydride in tetrahydrofuran (60.5 ml) was added dropwise to a portion of the above solid (3.5 g) suspended in tetrahydrofuran (150 ml) at 0° C., under nitrogen. The reaction mixture was warmed to ambient temperature and stirred overnight, under nitrogen. The reaction mixture was added to ice water, with stirring, and the mixture was extracted with 2-propanol/chloroform. The organic extracts were washed with water and brine, dried over anhydrous sodium sulfate, filtered, and the filtrate was concentrated. The residue was chromatographed on silica, eluting with 5% methanol/chloroform. The appropriate fractions were collected and evaporated to yield 1.2 g (32%) of product. The analytical sample was obtained by recrystallization from ethyl acetate/diethyl ether and had mp 152–153° C.

Analysis: Calculated for $C_{14}H_{15}N_3$: 74.64% C 6.71% H 18.65% N Found: 74.44% C 6.81% H 18.58% N

EXAMPLE 10

2,3-Dihydro-N-4-pyridinyl-1H-isoindol-2-amine hydrochloride

Phthalic anhydride (5.1 g) and 4-hydrazinopyridine hydrochloride (5.0 g) were suspended in glacial acetic acid (300 ml), and the mixture was heated under reflux for 8 hrs. The reaction mixture was evaporated, and the residue was triturated with 2-propanol. The solid was collected and dried to give 8.0 g of N-(4-pyridinylamino)-1H-isoindole. 1M lithium aluminum hydride in tetrahydrofuran (72.5 ml) was added dropwise to a portion (4.0 g) of the above solid suspended in tetrahydrofuran (200 ml) at 0° C., under nitrogen. The reaction mixture was warmed to ambient temperature, stirred overnight, under nitrogen, and was added to ice water, with stirring. The mixture was extracted with 2-propanol/chloroform (¼). The organic extracts were washed with water and brine, dried over anhydrous sodium sulfate, filtered, and the filtrate was concentrated. The residue was chromatographed on silica gel, eluting with 5% methanol/chloroform. The appropriate fractions were collected and evaporated to yield 1.3 g (36%) of product free base. The free base was dissolved in methanol, and methanolic hydrogen chloride was added. The precipitate was collected to give 0.25 g (5.8%) of product, mp 253–255° C.

Analysis: Calculated for $C_{13}H_{14}ClN_3$: 63.03% C 5.70% H 16.96% N Found: 62.47% C 5.63% H 16.72% N

EXAMPLE 11

1,4-Dihydro-2-[(N-4-pyridinyl)amino]-3-(2H)-isoquinolinone hydrochloride

Homophthalic anhydride (5 g) and 4-hydrazinopyridine hydrochloride (4.5 g) were suspended in glacial acetic acid (300 ml) and the mixture was heated under reflux for 8 hrs. The reaction mixture was evaporated, and the residue was triturated with 2-propanol. The solid was collected and dried to give 6.5 g (%) of 2-[(N-4-pyridinyl)amine]-1,3-(2H,4H)-isoquinolinedione hydrochloride. 1M lithium aluminum hydride in tetrahydrofuran (60.5 ml) was added dropwise to a portion (3.5 g) of 2-[(N-4-pyridinyl)amine]-1,3-(2H,4H)-isoquinolinedione hydrochloride suspended in tetrahydrofuran (150 ml) at 0° C., under nitrogen. The solution was warmed to ambient temperature, stirred overnight under nitrogen, and added to ice water, with stirring. The mixture was extracted with 2-propanol/chloroform. The organic extracts were washed with water and brine, dried over anhydrous sodium sulfate, filtered, and the filtrate was concentrated. The residue was chromatographed on silica, eluting with 5% methanol/chloroform. The appropriate fractions were collected and evaporated to yield 0.6 g (16.0%) of product free base. The free base was dissolved in methanol, and methanolic hydrogen chloride was added. The precipitate was collected to yield 0.22 g (6%) of product, mp 213–214° C.

Analysis: Calculated for $C_{14}H_{14}ClN_3O$: 60.98% C 5.12% H 15.24% N Found: 60.71% C 5.05% H 14.92% N

EXAMPLE 12

5-Bromo-2-(4-pyridinylamino-isoindole-1,3-dione hydrochloride

A solution of 5-bromophthalic anhydride (8.23 g), 4-hydrazinopyridine hydrochloride (5.2 g) in glacial acetic acid (180 ml) was heated under reflux for 6 hrs. The reaction mixture was allowed to cool to ambient temperature overnight. The precipitate was collected on a filter, washed with diethyl ether and dried in vacuo to give 8.32 g (65%) of product, mp>280° C.

Analysis: Calculated for $C_{13}H_9BrClN_3O_2$: 44.03% C 2.56% H 11.85% N Found: 44.39% C 2.74% H 11.83% N

EXAMPLE 13

4-Methoxy-2-(4-pyridinylamino)isoindole-1,3-dione hydrochloride hydrate

A solution of 3-methoxyphthalic anhydride (14.30 g), 4-hydrazinopyridine hydrochloride (11.12 g) and glacial acetic acid (75 ml) was heated under reflux overnight, with stirring. The reaction mixture was cooled to ambient temperature, the precipitate was collected arid washed with ether and the filtrate was evaporated. The residue was crystallized from ethanol, and the combined crops were dried at 60° C. under vacuum to give 19.8 g (80%) of product. The analytical sample was prepared by recrystallization from ethanol and had mp 203–205° C.

Analysis: Calculated for $C_{14}H_{14}ClN_3O_4$: 51.94% C 4.36% H 12.98% N Found: 52.33% C 4.34% H 12.84% N

EXAMPLE 14

5-Hydroxy-2-(4-pyridinylamino)isoindole-1,3-dione hydrochloride

A solution of 5-acetoxyphthalic anhydride (3.03 g), 4-hydrazinopyridine hydrochloride (2.04 g) and glacial acetic acid (15 ml) was heated under reflux, under nitrogen, for 4 hrs, with stirring. The reaction mixture was cooled to ambient temperature, the precipitate was collected, washed with water and dried at 60° C. under vacuum overnight. Trituration with hot absolute ethanol gave 2.3 g (56%) of product, mp >260° C.

Analysis: Calculated for $C_{13}H_{10}ClN_3O_3$: 53.53% C 3.46% H 14.41% N Found: 53.51% C 3.29% H 14.23% N

EXAMPLE 15

5-Bromo-2,3-dihydro-N-4-pyridinyl-1H-isoindol-2-amine hydrochloride

Lithium aluminum hydride (11.8 g) was added portionwise to a suspension of 5-bromo-2-(4-pyridinylamino-1(H)-isoindole-1,3(2H)-dione hydrochloride (22.2 g) in tetrahydrofuran (625 ml). The reaction mixture was stirred at ambient temperature for 18 hrs, sodium sulfate decahydrate was added, filtered, and the solvent was evaporated in vacuo. The residue was chromatographed on silica, eluting with triethyl amine, methanol and ethyl acetate. The appropriate fractions were collected and evaporated to provide 12.2 g (67%) of product, free base. A portion of the product free base (500 mg) was dissolved in methanol and treated with methanolic hydrochloride. Ether was added and the mixture was evaporated. The residue was recrystallized from methanol to give the analytical sample, mp 240°–265° C. (dec).

Analysis: Calculated for $C_{13}H_{13}BrClN_3$: 47.80% C 4.01% H 12.86% N Found: 48.03% C 3.85% H 12.83% N

EXAMPLE 16

2,3-Dihydro-4-methoxy-N-(-4-pyridinyl)-1H-isoindol-2-amine

A mixture of lithium aluminum hydride (9.96 g) in dry tetrahydrofuran (150 ml) was stirred at ambient temperature, under nitrogen, as 4-methoxy-2-(4-pyridinylamino) isoindole-1,3-dione hydrochloride monohydrate (17.0 g) was added in portions. The reaction mixture was stirred, under nitrogen, at ambient temperature overnight and sodium sulfate decahydrate was added in portions, with cooling. The precipitate was collected, washed with ethyl acetate, and the filtrate was evaporated. The residue was chromatographed on silica, eluting with 8–10% methanol-dichloromethane. The appropriate fractions were collected and concentrated. The residue was crystallized, then recrystallized from ethyl acetate to give 7.2 g (57%) of product, mp 144–146° C.

Analysis: Calculated for $C_{14}H_{15}N_3O$: 69.69% C 6.27% H 17.41% N Found: 69.67% C 6.31% H 17.39% N

EXAMPLE 17

N-[3-(3-Methoxyphenyl)propylidene]-N'-(4-pyridinyl)hydrazine hydrochloride

A slurry of 3-(3-methoxyphenyl)propionaldehyde (6.46 g), 4-hydrazinopyridine hydrochloride (6.30 g) and magnesium sulfate (5 g) in ethanol (75 ml) was heated under reflux, under nitrogen, with stirring, for 45 mins. The reaction mixture was filtered, the filter cake was washed with ethyl acetate, and the filtrate was concentrated in vacuo. The residue was triturated with ethyl acetate to give 7 g (61%) of product, mp 155–156° C.

Analysis: Calculated for $C_{15}H_{21}ClN_3O_1$: 61.75% C 6.22% H 14.40% N Found: 61.35% C 6.15% H 14.27% N

EXAMPLE 18

2,3-Dihydro-N-methyl-N-(4-pyridinyl)-1H-isoindol-2-amine hydrochloride

A solution of phthalic anhydride (2.53 g) and 1-methyl-1-(4-pyridinyl)hydrazine (2.0 g) in glacial acetic acid (10 ml) was heated under reflux, under nitrogen, 4 hrs, with stirring. The reaction mixture was evaporated, and the residue was azeotroped with heptane, dried under high vacuum to give 2-(4-pyridinylmethylamino)isoindole-1,3-dione. To a slurry of 2-(4-pyridinylmethylamino)isoindole-1,3-dione in tetrahydrofuran (75 ml) was added lithium aluminum hydride (3.08 g), in portions. The reaction mixture was stirred, under nitrogen, at ambient temperature overnight and sodium sulfate decahydrate was added in portions, with cooling. The precipitate was collected, washed with ethyl acetate, and the filtrate was evaporated. The residue was chromatographed on silica, eluting with 5–8% methanol/dichloromethane. The appropriate fractions were collected and evaporated. The residue was dissolved in absolute ethanol and concentrated hydrochloric acid was added. The precipitate was recrystallized from ethanol to give 720 mg (17%) of product, mp>260° C.

Analysis: Calculated for $C_{14}H_{16}ClN_3$: 64.24% C 6.16% H 16.05% N Found: 64.03% C 6.19% H 16.01% N

EXAMPLE 19

2,3-Dihydro-2-(4-pyridinylamino)-1H-isoindol-4-ol hydrobromide

A solution of 2,3-dihydro-4-methoxy-N-(4-pyridinyl)-1 H-isoindol-2-amine (6.10 g) in 48% hydrobromic acid (50 ml) was heated under reflux for 4 hrs, with stirring. The reaction mixture was cooled to about 10° C. and filtered. The filtrate was washed with cold water and dried under vacuum at 80° C. to give 6.1 g (78%) of product. The analytical sample was obtained by recrystallization from water (dried at 80° C. under vacuum) and had mp 249–252° C. (dec).

Analysis: Calculated for $C_{13}H_{13}N_3O\cdot HBr$: 50.67% C 4.58% H 13.63% N Found: 50.51% C 4.58% H 13.42% N

EXAMPLE 20

5-Hydroxy-2-(4-pyridinylmethylamino)isoindole-1,3-dione hydrochloride hemihydrate A solution of 5-acetoxyphthalic anhydride (15.65 g), 1-methyl-1-(4-pyridinyl)hydrazine (8.90 g) and glacial acetic acid (60 ml) was heated under reflux, under nitrogen, for 4 hrs, with stirring. The reaction mixture was cooled to ambient temperature, the precipitate was collected arid washed with ether. Trituration of the residue with absolute ethanol gave 16.2 g (83%) of product. Two grams of the residue were dissolved in absolute ethanol, treated with concentrated hydrochloric acid and cooled. The precipitate was collected and recrystallized from absolute ethanol (2 times) to give 1.4 g of product, mp>260° C., as the analytical sample.

Analysis: Calculated for $C_{14}H_{11}N_3O_3 \cdot HCl \cdot 0.5H_2O$: 53.43% C 4.16% H 13.35% N Found: 53.46% C 4.16% H 13.37% N

EXAMPLE 21

N-[2-(3-Methoxy-4-benzyloxyphenyl)-ethylidene]-N'-pyridin-4-yl-hydrazine hydrochloride To a stirred solution of 1-benzyloxy-2-methoxy-4-(2-methoxyvinyl)benzene (11.0 g), 4-hydrazinopyridine hydrochloride (6.6 g), and ethanol (150 ml) was added p-toluene sulfonic acid (0.39 g). The reaction mixture was stirred under reflux for 2 hrs and concentrated in vacuo. Recrystallization of the residue from methanol/ether gave 9.48 g (61%) of product, mp 154–155° C.

Analysis: Calculated for $C_{21}H_{23}Cl_2N_3O_2$: 65.71% C 5.78% H 10.95% N Found: 65.47% C 5.81% H 10.81% N

EXAMPLE 22

2,3-Dihydro-2-(4-pyridinylamino)-1H-isoindol-4-yl dimethylcarbamate

To a mixture of 2,3-dihydro-2-(4-pyridinylamino)-1H-isoindol-4-ol (1.20 g), triethylamine (1.18 g) and chloroform (35 ml), was added dimethylcarbamyl chloride (0.68 g) with stirring, at ambient temperature, under nitrogen. The reaction mixture was heated under reflux for 3 hrs, poured into dilute sodium bicarbonate solution (100 ml), and the layers were separated. The aqueous phase was extracted with chloroform, and the combined organic extracts were dried over anhydrous sodium sulfate, filtered, and the filtrate was evaporated. The residue was chromatographed on silica, eluting with 10–15% methanol/dichloromethane. The appropriate fractions were collected and concentrated to give 953 mg (60%) of product. Recrystallization from dichloromethane-heptane gave the analytical sample, mp 183–185° C.

Analysis: Calculated for $C_{16}H_{18}N_4O_2$: 64.41% C 6.08% H 18.78% N Found: 63.90% C 6.06% H 18.64% N

EXAMPLE 23

N-[3-(3-methoxy-4-t-butyldimethylsilyloxyphenyl) propylidene]-N'-pyridin-4-yl-hydrazine hydrochloride To a solution of ethyl 3-(4-hydroxy-3-methoxyphenyl) propionate (20.0 g) in dimethylformamide (150 ml) was added t-butyldimethylsilychloride (16.1 g) followed by imidazole (14.7 g). The reaction mixture was stirred for 2 hrs at ambient temperature, poured into water (1 l) and extracted with ethyl acetate (200 ml) followed by petroleum ether (500 ml). The combined organic extracts were dried over anhydrous magnesium sulfate, filtered, and the filtrate was concentrated in vacuo to afford 33.0 g of ethyl 3-(4-t-butyldimethylsilyoxy-3-methoxyphenyl)propionate as a colorless oil. To a slurry of lithium aluminum hydride (3.6 g) in tetrahydrofuran (200 ml) at 0° C. was added dropwise a solution of ethyl 3-(4-t-butyldimethylsilyoxy-3-methoxyphenyl)propionate in tetrahydrofuran (100 ml). The reaction mixture was stirred for 1 hr at 0° C. and sodium sulfate decahydrate was added. Ethyl acetate (500 ml) was added, and the mixture was filtered over celite. The filtrate was concentrated in vacuo to give 22.75 g of 3-(3-methoxy-4-t-butyldimethylsilyloxyphenyl)propon-1-ol. To a slurry of pyridinium chlorochromate (25.0 g) in dichloromethane (250 ml) at room temperature was added a solution of 3-(3-methoxy-4-t-butyldimethylsilyloxyphenyl)propon-1-ol in dichloromethane (100 ml). The reaction mixture was stirred for 1 hr and filtered through a bed of florisil. The filtrate was concentrated in vacuo to afford 17.0 g of 3-(3-methoxy-4-t-butyldimethylsilyloxyphenyl)propionyl aldehyde. To a solution of 3-(3-methoxy-4-t-butyldimethylsilyoxyphenyl)propionylaldehyde (10 g) in ethanol (100 ml) was added 4-hydrazinopyridine hydrochloride salt (5.4 g) followed by magnesium sulfate (5 g). The solution was heated under reflux for 1 hr, then filtered hot. The filtrate was concentrated in vacuo to afford 9.03 g (67%) of product, mp 147–149° C.

Analysis: Calculated for $C_{21}H_{32}ClN_3O_2Si$: 59.76% C 7.64% H 9.96% N Found: 58.99% C 7.67% H 10.39% N

EXAMPLE 24

[7-Methoxy-8-tert-butyldimethylsilyloxy-1,3,4,5-tetrahydrobenzo[c]azepine-2-yl]-pyridine-4-yl-amine To a solution of N-[3-(3-methoxy-4,6-butyldimethylsilyloxyphenyl)propylidene]-N'-pyridin-4-yl-hydrazine (5.81 g) in tetrahydrofuran (150 ml) was added lithium aluminum hydride in small portions at ambient temperature. The reaction mixture was stirred for 1.5 hrs at ambient temperature, sodium sulfate decahydrate was added. Ethyl acetate was added, and the mixture was filtered over celite. The filtrate was concentrated in vacuo to afford 5.81 g (75%) of N-[3-(3-methoxy-4-t-butyldimethylsilyloxyphenyl)propyl]-N'-pyridin-4-yl hydrazine. To a solution of N-[3-(3-methoxy-4-t-butyldimethylsilyloxyphenyl)propyl]-N'-pyridin-4-yl hydrazine in glacial acetic acid (50 ml) was added chloromethyl methyl ether (1.42 g). The reaction mixture was stirred overnight, then partitioned between 10% aqueous sodium hydroxide (500 ml) and ethyl acetate (500 ml). The organic extract was separated, dried over anhydrous magnesium sulfate, filtered, and the filtrate was concentrated in vacuo. This residue was chromatographed over silica gel, eluting with dichloromethane/methanol (9:1). The appropriate fractions were collected and evaporated to afford 3.61 g (60%) of product, mp 149–150° C.

Analysis: Calculated for $C_{22}H_{33}N_3O_2Si$: 66.13% C 8.32% H 10.52% N Found: 66.23% C 8.47% H 10.37% N

EXAMPLE 25

(7-Methoxy-1,3,4,5-tetrahydro-2-benzo[c]azepinyl)-4-pyridinylamine 0.2 hydrate To a solution of (N-[3-(3-methoxy phenyl)propylidine]-N-4-pyridinyl)hydrazine (12.0 g) in acetic acid (90 ml) was added a solution of chloromethyl methyl ether in acetic acid (10 ml). The reaction mixture was stirred overnight, under nitrogen, at ambient temperature, then heated at 50° C. for one hr. The reaction mixture was extracted with ethyl acetate, and the extract was washed with 10% sodium hydroxide solution and concentrated in vacuo. The residue was chromatographed on silica, eluting with 10% methanol:dichloromethane. The appropriate fractions were collected and concentrated to give 9.22 g (95%) of product. The analytical sample was prepared by recrystallization from dichloromethane, heptane and ether and had mp 120–121° C.

Analysis: Calculated for $C_{16}H_{19}N_3O.0.2\ H_2O$: 70.41% C 7.16% H 15.39% N Found: 70.69% C 7.03% H 15.63% N

EXAMPLE 26

7-Methoxy-2-(pyridin-4-yl-amino)-1,2,3,4-tetrahydroisoquinolin-6-ol-dihydrochloride A solution of (6-benzyloxy-7-methoxy-3,4-dihydro-1 H-isoquinolin-2-yl)pyridin-4-ylamine (2.0 g) in ethanol (75 ml) was slowly added to Degussa 5% palladium-on-carbon (0.1 g). The mixture was hydrogenated overnight at ambient temperature in a Parr Shaker at 55 psi. The reaction mixture was filtered through a pad of celite and the pad was washed with ethanol. The filtrate was concentrated, and the residue was purified by Chromatotron chromatography (5% methanol/ethyl acetate). The appropriate fractions were collected and concentrated. The residue was dissolved in hot methanol. Ethanolic hydrochloric acid was added and the precipitate was collected to yield 0.25 g (13%) of product, mp 194–195° C.

Analysis: Calculated for $C_{15}H_{17}N_3O_2.2HCl.0.39H_2O$: 51.28% C 5.69% H 11.96% N Found: 51.52% C 5.76% H 11.53% N

EXAMPLE 27

(3,4-Dihydro-6-methoxy-1H-isoquinolin-2-yl)-4-pyridinylamine hydrochloride

Lithium aluminum hydride (0.55 g) was added portionwise to a suspension of N-[2-(3-methoxyphenyl) ethylidene]-N'-pyridin-4-yl hydrazone (2.0 g) in tetrahydrofuran (36 ml) at 0° C. The reaction mixture was stirred at ambient temperature for 1 hr, sodium sulfate decahydrate was added. The mixture was filtered, and the filtrate was concentrated to give 1.73 g of N-[2-(3-methoxyphenyl) ethyl]-N'-pyridin-4-yl hydrazine. A solution of N-[2-(3-methoxyphenyl)ethyl]-N'-pyridin-4-yl hydrazine (0.85 g) and chloromethyl methyl ether (0.31 g) in acetic acid (15 ml) was heated at 55° C. for 1.5 hrs, and the mixture was cooled to 0° C. Sodium hydroxide solution (15%) was added and the mixture was extracted with ethyl acetate. The combined organic extracts were washed with water and brine, dried over anhydrous magnesium sulfate, filtered, and the filtrate was concentrated. The residue was dissolved in methanol and methanolic hydrogen chloride and then ether were added to give 0.31 g (30%) of product, mp 199–200° C.

Analysis: Calculated for $C_{15}H_{17}Cl_{18}N_3O$: 61.75% C 6.22% H 14.40% N Found: 61.41% C 6.21% H 14.31% N

EXAMPLE 28

(7-Methoxy-1,3,4,5-tetrahydrobenzo[c]azepin-4-yl) methyl-1-pyridin-4-yl-amine

To a solution of 3-(3-methoxyphenyl)propionaldehyde (9.75 g) in ethanol (100 ml) was added 4-(1-methylhydrazino)pyridine (9.80 g) and magnesium sulfate (10 g). The reaction mixture was heated under reflux for 1 hr, filtered hot, and the filtrate was concentrated in vacuo. The residue was chromatographed over silica gel, eluting with dichloromethane:methanol (9:1). The appropriate fractions were collected and evaporated to give 10.4 g (65%) of N-[3-(3-methoxyphenyl)propylidene]-N'pyridin-4-yl hydrazine. To a slurry of lithium aluminum hydride (3.38 g) in tetrahydrofuran (40 ml) was added N-[3-(3-methoxyphenyl) propylidine]-N'-pyridin-4-yl hydrazine (8.0 g) in small portions. The reaction mixture was stirred for 1 hr at ambient temperature, and sodium sulfate decahydrate was added. The slurry was diluted with ethyl acetate, and the mixture was filtered through celite. The filtrate was concentrated in vacuo to give 6.16 g (76%) of N-[3-(3-methoxyphenyl) propyl]N'-pyridin-4-yl hydrazine.

To a solution of N-[3-(3-methoxyphenyl)propyl]-N'-pyridin-4-yl hydrazine (6.0 g) in acetic acid was added chloromethyl methyl ether (2 ml) in one portion. The reaction mixture was stirred at ambient temperature for 1 hr, and at 50° C. for 2 hrs. The solution was then allowed to cool to ambient temperature, stirred overnight, and ethyl acetate (500 ml) was added. The organic phase was washed with aqueous 10% sodium hydroxide, separated, dried over anhydrous magnesium sulfate, filtered, and the filtrate was concentrated in vacuo. The residue was chromatographed over silica gel eluting with dichloromethane:methanol (9:1). The appropriate fractions were collected and evaporated to give 5.2 g (83%) of product, mp 163–165° C.

Analysis: Calculated for $C_{17}H_{21}N_3O$: 72.06% C 7.47% H 14.83% N Found: 71.89% C 7.46% H 14.72% N

EXAMPLE 29

N-[3-(Phenyl)propylidine]-N'-(4-pyridinyl)hydrazine hydrochloride

To a solution of hydrocinnamaldehyde (5.0 g) in ethanol (50 ml) was added 4-hydrazinopyridine (5.9 g) followed by magnesium sulfate (5 g). The reaction mixture was heated under reflux for 2.5 hrs, filtered, and the filtrate was concentrated in vacuo. The residue was triturated with hot ethyl acetate and filtered to give 9.0 g (92%) of product. Recrystallization from ethyl acetate and methanol gave the analytical sample, mp 204–205° C.

Analysis: Calculated for $C_{14}H_{16}ClN_3$: 64.24% C 6.16% H 16.05% N Found: 63.99% C 6.10% H 15.88% N

EXAMPLE 30

6-Methoxy-2-(pyridin-4-ylamino)-1,2,3,4-tetrahydro-isoquinolin-7-yl-dimethyl carbamate To a stirred solution of 6-(methoxy-7-hydroxy-3,4-dihydro-1 H-isoquinolin-2-yl)pyridin-4-yl-amine (1.07 g) triethylamine (1.2 ml) and chloroform (35 ml), dimethylcarbamyl chloride (0.44 ml) was added. The reaction mixture was heated under reflux for 2 hrs, with stirring, poured into saturated sodium bicarbonate solution (100 ml) and extracted with chloroform. The combined organic extracts were concentrated in vacuo, and the residue was chromatographed on silica gel eluting with 20% methanol/dichloromethane. The appropriate fractions were collected and concentrated in vacuo to yield 0.310 g (23%) of product, mp 176–177° C.

Analysis: Calculated for $C_{18}H_{22}N_4O_3.0.33H_2O$: 62.05% C 6.56% H 16.08% N Found: 61.85% C 6.45% H 15.43% N

EXAMPLE 31

2-(4-Pyridinylamino)-1,2,3,4-tetrahydroisoquinolin-6-yl dimethyl carbamate

Dimethyl carbamoyl chloride (0.50 g) was added dropwise to an ambient temperature mixture of (6-hydroxy-1,2, 3,4-tetrahydro-1H-isoquinolin-2-yl)-4'-pyridinylamine (0.93 g) and triethylamine (0.85 g) in chloroform (25 ml). The reaction mixture was heated under reflux for 4 hrs, cooled and poured into saturated sodium bicarbonate solution. The layers were separated, and the aqueous phase was extracted with dichloromethane. The combined organic extracts were washed with water and brine, dried over anhydrous magnesium sulfate, filtered, and the filtrate was concentrated to give 0.97 g (%) of product. The product was chromatographed on silica gel using a chromatochron, eluting with 2% triethylamine/23% methanol/75% ethyl acetate. The appropriate fractions were collected and evaporated to provide 0.34 g (28%) of the analytical sample, mp 208–211° C.

Analysis: Calculated for $C_{17}H_{20}N_4O_2$: 65.37% C 6.45% H 17.94% N Found: 64.87% C 6.40% H 17.66% N

EXAMPLE 32

N'-[3-(4-methoxyphenyl)propylidene]-N-methyl-N-pyridin-4-yl hydrazine hydrochloride To a solution of 3-(methoxyphenyl)propionaldehyde (6.0 g) in ethanol (50 ml) was added 1-methyl-1-(4-pyridyl) hydrazine (4.5 g) followed by anhydrous magnesium sulfate (5 g). The reaction mixture was heated under reflux, with stirring for 1 hr, filtered hot, and the filtrate was concentrated in vacuo. The residue was chromatographed over silica gel eluting with dichloromethane:methanol (9:1). The appropriate fractions were collected and concentrated to afford 6.4 g (57%) of product, mp 163–165° C.

Analysis: Calculated for $C_{16}H_{20}ClN_3O$: 62.84% C 6.59% H 13.74% N Found: 63.00% C 6.47% H 13.51% N

EXAMPLE 33

N-[2-(4-Benzyloxyphenyl)ethylidene]-N'-pyridin-4-ylhydrazine hydrochloride monohydrate A mixture of 1-benzyloxy-4-(2-methoxyvinyl)benzene (16.9 g), 4-hydrazinopyridine hydrochloride (11.3 g) and p-toluenesulfonic acid (0.68 g) in ethanol (200 ml) was heated under reflux for 5 hrs, with stirring. The reaction mixture was cooled, filtered, and the filtrate was concentrated in vacuo. The residue crystallized to give 15.75 g (63%) of product, mp 203–205° C.

Analysis: Calculated for $C_{20}H_{19}N_3O \cdot H_2O \cdot HCl$: 64.60% C 5.96% H 11.30% N Found: 64.53% C 5.88% H 11.46% N

EXAMPLE 34

N-[2-(4-benzyloxyphenyl)ethyl]-N'-pyridin-4-yl-hydrazine hydrochloride

Lithium aluminum hydride (0.43 g) was added portionwise to a suspension of N-[2-(4-benzyloxyphenyl)ethylidene]-N'-pyridin-4-ylhydrazine hydrochloride (2.0 g) in tetrahydrofuran (28 ml) at 0° C. The reaction mixture was stirred at ambient temperature for 1 hr, and sodium sulfate decahydrate was added. The mixture was filtered, and the filtrate was evaporated to provide 1.66 g of product free base. A portion (0.66 g) of the free base was dissolved in hot ethanol, and methanolic hydrogen chloride was added. The precipitate was collected to provide 0.38 g (48%) of product, mp 231–233° C.

Analysis: Calculated for $C_{20}H_{21}N_3O \cdot HCl$: 67.50% C 6.23% H 11.81% N Found: 67.27% C 6.12% H 11.64% N

EXAMPLE 35

7-(Benzyloxy-3,4-dihydro-1H-isoquinolin-2-yl)-4-pyridinylamine

Lithium aluminum hydride (2.76 g) was added portionwise to a suspension of N-[2-(4-benzyloxyphenyl)ethyl]-N'-pyridin-4-yl hydrazone hydrochloride (12.87 g) in tetrahydrofuran (180 ml), at 0° C. The reaction mixture was stirred at ambient temperature for 18 hrs, and sodium sulfate decahydrate was added. The mixture was filtered, and the filtrate was evaporated to provide 11.0 g of N-[2-(4-benzyloxyphenyl)ethyl]-N'-pyridin-4-yl hydrazine. A solution of N-[2-(4-benzyloxyphenyl)ethyl]-N'-pyridin-4-yl hydrazine and chloromethyl methyl ether (3.04 g) in acetic acid (140 ml) was heated under reflux for 1 hr and then poured into ice. Sodium hydroxide solution (50%) was added and the mixture was extracted with ethyl acetate. The combined organic extracts were washed with water and brine, dried over anhydrous magnesium sulfate, filtered, and the filtrate was concentrated. The residue was chromatographed on silica gel using a high performance chromatography system, eluting with 10% methanol/ethyl acetate. The appropriate fractions were collected and evaporated to yield 8.1 g (71%) of product, mp 138–140° C.

Analysis: Calculated for $C_{21}H_{21}N_3O$: 76.11% C 6.39% H 12.68% N Found: 75.45% C 6.45% H 12.64% N

EXAMPLE 36

2-(4-Pyridinylamino)-1,2,3,4-tetrahydroisoquinolin-7-yl dimethyl carbamate

Dimethyl carbamoyl chloride (0.80 g) was added dropwise to a mixture of 2-(pyridin-4-yl amino)-1,2,3,4-tetrahyroisoquin-7-ol (1.5 g) and triethylamine (1.83 g) in chloroform (65 ml) at ambient temperature. The reaction mixture was heated under reflux for 5 hrs, allowed to cool and poured into saturated sodium bicarbonate solution. The layers were separated and the aqueous phase was extracted with dichloromethane. The combined organic extracts were washed with water and brine, dried over anhydrous magnesium sulfate, filtered, and the filtrate was concentrated. The residue was chromatographed on silica gel using a Chromatotron, eluting with 2% triethylamine/23% methanol/75% ethyl acetate. The appropriate fractions were collected and evaporated to provide 1.65 g (85%) of product. Recrystallization from methanol gave the analytical sample, mp 204–205° C.

Analysis: Calculated for $C_{17}H_{20}N_4O_2$: 65.37% C 6.45% H 17.94% N Found: 65.02% C 6.40% H 18.16% N

EXAMPLE 37

7-Methoxy-2(4-pyridinylamino)-1,2,3,4-tetrahydroisoquinolin-6-yl dimethyl carbamate Dimethyl carbamoyl chloride (0.81 ml) was added dropwise to a mixture of 7-methoxy-2-(pyridin-4-yl amino)-1,2,3,4-tetrahydroisoquinolin-6-ol (92 g) and triethylamine (2.3 ml) in chloroform (75 ml) at ambient temperature. The reaction mixture was heated under reflux for 0.5 hr, stirred overnight at ambient temperature and was added to sodium bicarbonate solution and chloroform. The layers were separated and the organic extract was washed with water and brine, dried over anhydrous magnesium sulfate, filtered, and the filtrate was concentrated. The residue was chromatographed on silica gel, eluting with 1% triethylamine, 5% methanol, 94% ethyl acetate; ended with 1% triethylamine, 20% methanol, 79% ethyl acetate. The appropriate fractions were collected and evaporated to yield 2.1 g (83%) of product, mp 210° C.

Analysis: Calculated for $C_{18}H_{22}N_4O_3$: 63.14% C 6.48% H 16.36% N Found: 62.88% C 6.47% H 16.04% N

EXAMPLE 38

N-[3-(4-methoxyphenyl)propylidene]-N'-(4-pyridyl) hydrazine hydrochloride hemihydrate To a solution of 3-(4-methoxyphenyl)propionaldehyde (5.0 g) in ethanol (100 ml) was added 4-hydrazinopyridine hydrochloride (4.42 g), followed by magnesium sulfate (5 g). The solution was heated under reflux for 1 hr, cooled to ambient temperature and filtered. The filtrate was concentrated in vacuo and the residue was chromatographed over silica gel eluting with dichloromethane:methanol (9:1). The appropriate fractions were collected and concentrated to afford 7.2 g (81%) of product, mp 164–165° C.

Analysis: Calculated for $C_{15}H_{18}ClN_3O\cdot0.5\ H_2O$: 59.90% C 6.37% H 13.97% N Found: 60.00% C 6.13% H 14.39% N

EXAMPLE 39

[7-Methoxy-8-hydroxy-1,3,4,5-tetrahydrobenzo[c] azepine-2-yl]pyridin-4-yl amine hydrochloride 0.25 hydrate To a solution of [7-methoxy-8-t-butyldimethylsilyloxy-1, 3,4,5-tetrahydrobenzo[c]azepine-2yl]pyridin-4-yl-amine (7.84 g) in tetrahydrofuran (100 ml) at 0° C. was added 1 M tetrabutylammonium fluoride (23.5 ml) in tetrahydrofuran. The reaction mixture was allowed to warm to ambient temperature, stirred overnight and dichloromethane (500 ml) was added. The organic extracts were washed with water, separated, dried over anhydrous magnesium sulfate, and the filtrate was concentrated in vacuo. The residue was chromatographed on silica gel, eluting with dichloromethane:methanol (8:1). The appropriate fractions were collected and concentrated. The residue was dissolved in methanol (30 ml), and concentrated hydrochloric acid was added. The solution was concentrated in vacuo. The residue was crystallized from dichloromethane-methanol to afford 1.6 g (25%) of product, mp 199–210° C.

Analysis: Calculated for $C_{16}H_{20}ClN_3O_2\cdot0.25\ H_2O$: 58.89% C 6.33% H 12.88% N Found: 58.82% C 6.70% H 12.46% N

EXAMPLE 40

(1.3-Dihydroisoindol-2-yl)-(3-fluoropyridin-4-yl) amine hydrochloride

To a stirred solution of phthalic anhydride (1.76 g) in acetic acid (45 ml), 3-fluoro-4-hydrazinopyridine (1.52 g) was added. The reaction mixture was heated under reflux for 1 hr and concentrated in vacuo to give 3.88 g of 2-(3-fluoropyridin-4-ylamino)isoindole-1,3-dione. To a stirred solution of 2-(3-fluoropyridin-4-ylamino)isoindole-1,3-dione (3.88 g) in tetrahydrofuran (125 ml) at 0° C., lithium aluminum hydride (2.86 g) was added. The reaction mixture was allowed to warm to ambient temperature and was stirred for 1 day. Sodium sulfate decahydrate was added, and the mixture was filtered. The filtrate was concentrated in vacuo. The residue was chromatographed on a silica gel eluting with ethyl acetate. The appropriate fractions were collected and concentrated to yield 1.28 g (37%) of product free base.

A portion of the free base was dissolved in methanol, and ethereal hydrogen chloride was added. The precipitate was collected and recrystallized from methanol to yield 0.200 g of product, mp 200–202° C.

Analysis: Calculated for $C_{13}H_{13}ClFN_3$: 58.76% C 4.93% H 15.81% N Found: 58.66% C 5.15% H 15.54% N

EXAMPLE 41

Dimethylcarbamic acid-2-(4-pyridinylamino)-2,3,4, 5-tetrahydro-1H-benzo[c]azepin-7-yl ester hydrochloride 0.25 hydrate To a solution of (7-methoxy-1,3,4,5-tetrahydro-2-benzo [c]azepinyl)-4-pyridinylamine in dichloromethane (50 ml) was added boron tribromide (3.9 ml) at 0° C. The reaction mixture was stirred for 2 hrs at ambient temperature, methanol was added, and the mixture was concentrated in vacuo to afford (7-hydroxy-1,3,4,5-tetrahydro-2-benzo[c]azepinyl-4-pyridinylamine hydrobromide. (7-Hydroxy- 1,3,4,5-tetrahydro-2-benzo[c]azepinyl-4-pyridinylamine hydrobromide was neutralized with sodium bicarbonate solution to afford 1.3 g of (7-hydroxy-1,3,4,5-tetrahydro-2-benzo[c] azepinyl-4-pyridinylamine. To a solution of (7-hydroxy-1, 3,4,5-tetrahydro-2-benzo[c]azepinyl-4-pyridinylamine (1.2 g) in chloroform (30 ml) was added dimethyl carbamyl chloride (0.48 ml) followed by triethylamine (1.43 ml). The reaction mixture was heated under reflux, with stirring, for 2 hrs, allowed to cool to ambient temperature, and dichloromethane (200 ml) was added. The organic extract was washed with saturated sodium bicarbonate (100 ml), dried over anhydrous magnesium sulfate, filtered, and the filtrate was concentrated in vacuo. The residue was chromatographed over silica gel, eluting with dichloromethane:methanol (9:1). The appropriate fractions were collected and concentrated. The residue was dissolved in methanol, acidified with concentrated hydrochloric acid, and concentrated in vacuo. The residue was triturated with petroleum ether and filtered to give 0.72 g (44%) of product, mp 100–110° C.

Analysis: Calculated for $C_{18}H_{23}ClN_4O_2\cdot0.25H_2O$: 58.85% C 6.45% H 15.25% N Found: 58.75% C 6.32% H 15.34% N

EXAMPLE 42

2-(3-Fluoro-4-methoxyphenyl)-4-4-dimethyl-4,5-dihydrooxazole

To a slurry of 3-fluoro-4-methoxybenzoic acid (30.0 g) in toluene (100 ml) was added thionyl chloride (25 ml). The reaction was heated under reflux for 2 hrs and then distilled. The residue was dried under high vacuum to give 32 g of 3-fluoro-4-methoxybenzoyl chloride. To a solution of 2-amino-2-methyl-1-propanol (35 ml) in dichloromethane (200 ml) was added a solution of the 3-fluoro-4-methoxybenzoyl chloride in dichloromethane (150 ml). The reaction mixture was stirred for 1 hr at ambient temperature, dichloromethane (500 ml) was added, and washed with 2N hydrochloric acid (1 l). The layers were separated and the organic extract was dried over anhydrous magnesium sulfate, filtered, and the filtrate was concentrated in vacuo. To the residue was added thionyl chloride (25 ml) at 0° C. The reaction mixture was stirred for 30 min, diethyl ether (200 ml) was added, and the mixture was stirred for 10 min. The supernatant was decanted. 10% Sodium hydroxide solution was added, and the mixture was extracted with ethyl acetate. The organic extracts were combined, dried over anhydrous magnesium sulfate, filtered, and the filtrate was concentrated in vacuo to give 36 g (91%) of product, mp 59–60° C.

Analysis: Calculated for $C_{12}H_{14}FNO_2$: 64.56% C 6.32% H 6.27% N Found: 64.35% C 6.35% H 6.11% N

EXAMPLE 43

2,3-Dihydro-5-methoxy-N-(4-pyridinyl)-1H-isoindol-2-amine

A mixture of 5-methoxyisobenzofuran-1,3-dione (33.0 g), 4-pyridinylhydrazine hydrochloride (25.7 g) and glacial acetic acid (100 ml) was heated overnight, under reflux, under nitrogen, with stirring. Water (100 ml) was added, and the mixture was evaporated and dried in vacuo. The residue was triturated with acetone, the acetone decanted, and the residue was triturated with methanol to give 16.1 g of 5-methoxy-2-(4-pyridinylamino)isoindol-1,3-dione. To a mixture of lithium aluminum hydride (6.00 g) and dry tetrahydrofuran (150 ml) at ambient temperature, under nitrogen, 5-methoxy-2-(4-pyridinylamino)isoindol-1,3-dione hydrochloride (16.1 g) was added in portions, with stirring. The reaction mixture was stirred at room temperature, under nitrogen, 4 hrs, and sodium sulfate decahydrate was added in portions. The mixture was filtered through a bed of celite, the filter cake was washed thoroughly with ethyl acetate, and the filtrate was concentrated in vacuo. The residue was chromatographed over silica gel, eluting with 7% methanol-dichloromethane followed by 185:14:1 dichloromethane:methanol:ammomium hydroxide. The appropriate fractions were collected and concentrated. The residue was crystallized from ethanol to give 5.8 (46%) of product, mp 166–167° C.

Analysis: Calculated for $C_{14}H_{15}N_3O$: 69.69% C 6.27% H 17.41% N Found: 69.69% C 6.34% H 17.37% N4

EXAMPLE 44

7-Methoxy-2-(4-pyridinylamino)-4H-isoquinoline-1,3-dione hydrochloride hemihydrate A solution of 7-methoxyisochroman-1,3-dione (4.50 g), 4-hydrazinopyridine hydrochloride (3.25 g) and glacial acetic acid (35 ml) was heated under reflux, under nitrogen, for 4 hrs, with stirring. The reaction mixture was allowed to cool to ambient temperature, and the precipitate was collected and washed with ether. The filter cake was recrystallized from absolute ethanol, dried at 100° C. under vacuum to give 1.55 g (21%) of product, mp 218–223° C.

Analysis: Calculated for $C_{15}H_{13}N_3O_3.0.5 H_2O$: 54.80% C 4.60% H 12.78% N Found: 54.34% C 4.54% H 12.73% N

EXAMPLE 45

2.3-Dihydro-2-(4-pyridinylamino)-1H-isoindol-4-yl-1,2,3,4-tetrahydroisoquinolin-2-ylcarbamate hydrochloride To a mixture of 2,3-dihydro-2-(4-pyridinylamino)-1H-isoindol-4-ol (1.50 g), triethylamine (1.47 g) and chloroform (20 ml) at ambient temperature, under nitrogen, 1,2,3,4-tetrahydroisoquinolin-2-ylcarbamyl chloride (1.55 g) in chloroform (10 ml) was added with stirring. The reaction mixture was heated under reflux for 1 hr, poured into dilute sodium bicarbonate solution (100 ml), and the layers were separated. The aqueous phase was extracted with chloroform, and the combined organic extracts were dried over anhydrous sodium sulfate, filtered, and the filtrate was evaporated in vacuo. The residue was chromatographed on silica, eluting with 10–15% methanol-dichloromethane, and then on silica, eluting with 90:9:1 dichloromethane:methanol:ammonium hydroxide. The appropriate fractions were collected and concentrated to give 1.78 g (70%) of product, free base. The free base was dissolved in absolute ethanol, and concentrated hydrochloric acid was added. The solution was cooled, the precipitate was collected, recrystallized from absolute ethanol and dried under vacuum at 80° C. to give 950 mg (34%) of product, mp 242–245° C.

Analysis: Calculated for $C_{23}H_{23}ClN_4 O_2$: 65.32% C 5.48% H 13.25% N Found: 65.06% C 5.39% H 13.15% N

EXAMPLE 46

2,3-Dihydro-2-(4-pyridinylamino)-1H-isoindol-5-ol hydrobromide

A solution of 2,3-dihydro-5-methoxy-N-(4-pyridinyl)-1 H-isoindol-2-amine (5.25 g) in 48% hydrobromic acid (35 ml) was heated under reflux for 5 hrs, with stirring. The reaction mixture was cooled to about 10° C. and filtered. The filter cake was washed with cold water and dried under vacuum in an oven at 80° C. to give 4.8 g (72%) of product. The product was recrystallized from water and dried under vacuum at 80° C. to give 3.1 g (46%) of the analytical sample, mp 261–264° C.

Analysis: Calculated for $C_{13}H_{14}BrN_3O$: 50.67% C 4.58% H 13.63% N Found: 50.81% C 4.37% H 13.60% N

EXAMPLE 47

2-[Methyl(pyridin-4-yl)amino]-1,2,3,4-tetrahydro-isoquinolin-6-ol

A mixture of 6-benzyloxy-3,4-dihydro-1H-isoquinoline-2-yl-N-methyl-4-pyridinylamine (5.1 g) and 5% palladium-on-carbon (1.0 g) in methanol (75 ml) was shaken on a Parr hydrogenation apparatus at ambient temperature and an initial pressure of 55 psi for 2 hrs. An additional 1 g of catalyst was added, and the mixture was shaken for an additional 4 hrs at an initial pressure of 55 psi. The reaction mixture was filtered through a pad of celite, the pad was washed with methanol, and the filtrate was concentrated to give 3.45 g (92%) of product. Recrystallization from methanol provided the analytical sample, mp 263–266° C.

Analysis: Calculated for $C_{15}H_{17}N_3O$: 70.56% C 6.71% H 16.46% N Found: 70.38% C 6.66% H 16.57% N

EXAMPLE 48

(6-Fluoro-7-methoxy-3,4-dihydro-1H-isoquinolin-2-yl)-4-pyridinylamine

Lithium aluminum hydride (4.5 g) was added portionwise to a suspension of the N-[2-(3-fluoro-5-methoxyphenyl) ethylidene]-N'-4-hydrazine hydrochloride (16.8 g) in tetrahydrofuran (300 ml) at 0° C. The reaction mixture was stirred at ambient temperature for 1 hr, and sodium sulfate decahydrate was added. The mixture was filtered and was concentrated to provide 15.1 g of N-[2-(3-fluoro-5-methoxyphenyl)ethyl]-N-pyridin-4-yl hydrazine. A solution of N-[2-(3-fluoro-5-methoxyphenyl)ethyl]-N-pyridin-4-yl hydrazine (15.1 g) and chloromethyl methyl ether (5.3 g) in acetic acid (240 ml) was heated under reflux for 2 hrs and then cooled to 0° C. 50% Sodium hydroxide solution was added, and the mixture was extracted with ethyl acetate. The combined organic extracts were washed with water and brine, dried over anhydrous magnesium sulfate, filtered, and the filtrate was concentrated. The residue was recrystallized from methanol to provide 3.5 g (23%) of product, mp 216–218° C.

Analysis: Calculated for $C_{15}H_{16}FN_3O$: 65.92% C 5.90% H 15.37% N Found: 65.65% C 5.83% H 15.29% N

EXAMPLE 49

Dimethylcarbamic acid-7-methoxy-2-(4-pyridinylamino)-2,3,4,5-tetrahydro-1H-benzo[c]azepin-8-yl ester hydrochloride To a solution of [7-methoxy-8-hydroxy-1,3,4,5-tetrahydrobenzo[c]azepin-2-yl]-4-pyridinylamine hydrochloride 0.25 hydrate (500 mg) in chloroform (10 ml) was added dimethylcarbamyl chloride (170 μl) and triethylamine (0.75 ml). The reaction mixture was heated under reflux for 3 hrs, then cooled to room temperature, and dichloromethane (200 ml) and saturated sodium bicarbonate solution (100 ml) were added. The aqueous phase was extracted with dichloromethane (2×5 ml), the organic extracts were combined, dried over anhydrous magnesium sulfate, filtered, and the filtrate was concentrated in vacuo. The residue was chromatographed over silica gel eluting with dichloromethane:methanol (9:1). The appropriate fractions were collected and concentrated. The residue was dissolved in methanol (5 ml), and concentrated hydrochloric acid was added. The mixture was concentrated in vacuo, and the residue was crystallized from diethyl ether-dichloromethane to give 320 mg (52%) of product, mp 95–110° C.

Analysis: Calculated for $C_{19}H_{25}ClN_4O_3$: 58.09% C 6.41% H 14.26% N Found: 57.68% C 6.36% H 14.45% N

EXAMPLE 50

N-[2-(2-Bromo-5-methoxyphenyl)ethylidene]-N'-pyridin-4-yl-hydrazine

A mixture of 4-bromo-1-methoxy-3-(2-methoxyvinyl) benzene (42.3 g), 4-hydrazinopyridine (27.6 g), and p-toluenesulfonic acid (3.3 g) in ethanol (500 ml) was heated under reflux overnight, with stirring. The reaction mixture was filtered, and the filtrate was concentrated to about 50% of its initial volume. The precipitate was collected to give 5.5 g of product, as the hydrochloride salt, and the filtrate was concentrated. Saturated sodium hydrogen carbonate solution was added to the residue and the mixture was extracted with ethyl acetate. The organic extract was dried over anhydrous magnesium sulfate, filtered, and the filtrate was concentrated. The residue was chromatographed on a Waters LC2000 instrument, gradient eluting with: 1% ethylamine/2% methanol/97% ethyl acetate/1% triethylamine acid/5% methanol/94% ethyl acetate. The appropriate fractions were collected and concentrated to yield 4.9 g (8.8%) of product, mp 142° C.

Analysis: Calculated for $C_{14}H_{14}BrN_3O$: 52.52% C 4.41% H 13.12% N Found: 52.57% C 4.42% H 13.03% N

EXAMPLE 51

(5-Bromo-3,4-dihydro-8-methoxy-1H-isoquinolin-2-yl)-4-pyridinylamine

Lithium aluminum hydride (1.3 g) was added portionwise to a suspension of N-[2-bromo-5-methoxyphenyl)ethylidene]-N-pyridin-4-ylhydrazone hydrochloride (8.4 g) in tetrahydrofuran (450 ml) at 0° C. The reaction mixture was stirred overnight at ambient temperature. Sodium sulfate decahydrate was added, and the mixture was filtered. The filtrate was concentrated, and the residue was chromatographed on a Waters C2000 instrument, gradient eluting with: 1% triethylamine/2% methanol/97% ethyl acetate; 1% triethylamine/5% methanol/94% ethyl acetate. The appropriate fractions were collected and concentrated to yield 6.9 g (91%) of N-[3-(2-bromo-5-methoxyphenyl)propyl]-N-pyridin-4-yl hydrazine. A solution of N-[3-(2-bromo-5-methoxyphenyl)propyl]-N-pyridin-4-yl hydrazine (96.6 g), chloromethyl methyl ether (1.7 ml) and acetic acid (400 ml) was heated under reflux for 1 hr. The reaction mixture was cooled, poured onto ice, and saturated sodium bicarbonate solution was added. The mixture was extracted with ethyl acetate, and the combined organic extracts were washed with water and brine, dried over anhydrous magnesium sulfate, filtered, and the filtrate was concentrated. The residue was chromatographed on a Waters LC2000 instrument, gradient eluting with 1% triethylamine/4% methanol/95% ethyl acetate. The appropriate fractions were collected and concentrated to provide 5.5 g (80%) of product, mp 172–173° C.

Analysis: Calculated for $C_{15}H_{16}BrN_3O$: 53.91% C 4.83% H 12.57% N Found: 54.04% C 4.73% H 12.53% N

EXAMPLE 52

(3.4-Dihydro-8-methoxy-1H-isoquinolin-2-yl)-4-pyridinylamine

A mixture of 5-bromo-3,4-dihydro-8-methoxy-1H-isoquinolin-2-yl-4-pyridinylamine (0.8 g), ethanol (75 ml) and 5% palladium-on-carbon (0.1 g) was hydrogenated at 55 psi overnight in a Parr shaker at ambient temperature. The reaction mixture was filtered through a pad of celite, the pad was washed with methanol, and the filtrate was concentrated. Aqueous sodium hydrogen carbonate was added to the residue, and the mixture was extracted with ethyl acetate. The extracts were dried over anhydrous magnesium sulfate, filtered, and the filtrate was concentrated. The residue was chromatographed on silica gel on a Chromatotron, eluting with 1% triethylamine/5% methanol/94% ethyl acetate. The appropriate fractions were collected and concentrated. The residue was crystallized in hot ethyl acetate to give 0.25 g (41%) of product, mp 170–171° C.

Analysis: Calculated for $C_{15}H_{17}N_3O$: 70.56% C 6.71% H 16.46% N Found: 70.39% C 6.74% H 16.35% N

EXAMPLE 53

N-[2-(2-fluoro-5-methoxy-phenyl)ethylidene]-N'-pyridin-4-yl-hydrazine hydrochloride To a solution of 1-fluoro-4-methoxy-2-(2-methoxyvinyl) benzene (20 g) and 4-hydrazinopyridine hydrochloride (17.7 g) in ethanol (300 ml), p-toluene sulfonic acid (3.13 g) was added, with stirring. The reaction mixture was stirred under reflux for 2 hrs, filtered, and the filtrate was concentrated in vacuo. The residue was recrystallized from methanol to yield 13.24 g (41%) of product, mp 219–220° C.

Analysis: Calculated for $C_{14}H_{15}ClN_3O$: 56.86% C 5.11% H 14.21% N Found: 56.65% C 5.09% H 14.11% N

EXAMPLE 54

N-[2-(4-methoxy-3-methyl-phenyl)ethylidene]-N'-pyridin-4-ylhydrazine hydrochloride To a solution of 1-methoxy-2-methyl-4-(2-methoxyvinyl) benzene (17 g) and 4-hydrazinopyridine hydrochloride (15.4 g) in ethanol (300 ml), p-toluenesulfonic acid (2.7 g) was added, with stirring. The reaction mixture was stirred under reflux for 2 hrs, filtered, and the filtrate was concentrated in vacuo. The residue was recrystallized from methanol to yield 10.9 g (39%) of product, mp 224–226° C.

Analysis: Calculated for $C_{15}H_{18}ClN_3O$: 61.75% C 6.22% H 14.40% N Found: 61.72% C 6.18% H 14.41% N

EXAMPLE 55

6-Fluoro-2-(4-pyridinylamino)-1,2,3,4-tetrahydroisoquinolin-7-ol hydrobromide Boron tribromide (8.8 g) was added dropwise to a solution of 6-fluoro-7-methoxy-2-(4-pyridinylamino)-1,2,3,4-tetrahydroisoquinoline (2.9 g) in dichloromethane (200 mL) at –78° C. The dry ice bath was removed, and the suspension was stirred at ambient temperature for 3 hrs. The reaction mixture was cooled to –78° C., and methanol (100 mL) was added. The mixture was stirred at ambient temperature for 1 hr and concentrated in vacuo. The residue was washed with methanol/ethyl ether and recrystallized from 2-propanol/ethyl acetate to give 0.61 g (17%) of product, mp 244–245° C. (dec).

Analysis: Calculated for $C_{14}H_{15}BrFN_3O$: 49.43% C 4.44% H 12.35% N Found: 49.41% C 4.32% H 12.16% N

EXAMPLE 56

6-Fluoro-2-(4-pyridinylamino)-1,2,3,4-tetrahydroisoquinolin-7-yl dimethyl carbamate Dimethyl carbamoyl chloride (0.46 g) was added dropwise to a mixture of 6-fluoro-2-(4-pyridinylamino)-1,2,3,4-tetrahydroisoquinoline-7-ol hydrobromide (1.5 g) and triethylamine (1.87 g) in chloroform (50 mL) at ambient temperature. The reaction mixture was heated under reflux for 3 hrs, cooled and poured into saturated sodium bicarbonate solution. The layers were separated, and the organic extract was extracted with dichloromethane. The extracts were washed with water and brine, dried over anhydrous magnesium sulfate, filtered, and the filtrate was concentrated. The residue was chromatographed on a Chromatotron, eluting with 2% triethylamine/23% methanol/75% ethyl acetate. The appropriate fractions were collected and concentrated to provide 0.93 g (79%) of product. The product was dissolved in ethyl acetate and the solution was washed with 10% sodium hydroxide solution. The layers were separated, and the organic layer was concentrated in vacuo. Recrystallization of the residue from methanol gave the analytical sample, mp 174–175° C.

Analysis: Calculated for $C_{17}H_{19}FN_4O_2$: 61.81% C 5.80% H 16.96% N Found: 61.41% C 5.67% H 16.91% N

EXAMPLE 57

(8-Chloro-4-methoxy-3,4-dihydro-1H-isoquinolin-2-yl)-4-pyridinylamine

Lithium aluminum hydride (3.3 g) was added portionwise to a suspension of N-[2-(5-chloro-2-methoxyphenyl)ethylidine]-N-pyridin-4-ylhydrazine hydrochloride (13.4 g) in tetrahydrofuran (215 mL) at 0° C. The reaction mixture was stirred at ambient temperature for 2 hrs, and sodium sulfate decahydrate was added. The mixture was filtered, and the filtrate was concentrated to provide 11.8 g of N-[2-(5-chloro-2-methoxyphenyl)ethyl]-N-pyridine-4-ylhydrazine, as an oil. A solution of N-[2-(5-chloro-2-methoxyphenyl)ethyl]-N-pyridine-4-ylhydrazine (11.8 g) and chloromethyl methyl ether (3.8 g) in acetic acid (170 mL) was heated under reflux for 2 hrs and then cooled to 0° C. Sodium hydroxide solution (50%) was added, and the mixture was extracted with ethyl acetate. The combined organic layers were washed with water and brine, dried over anhydrous magnesium sulfate, filtered, and the filtrate was concentrated. The residue was chromatographed on silica gel, eluting with 10% methanol/ethyl acetate. The appropriate fractions were collected and concentrated to provide 6.54 g (52%) of product. Recrystallization from ethyl acetate provided the analytical sample, mp 152–154° C. (dec).

Analysis: Calculated for $C_{15}H_{16}ClN_3O$: 62.18% C 5.57% H 14.50% N Found: 61.95% C 5.63% H 14.24% N

EXAMPLE 58

8-Chloro-2-(4-pyridinylamino)-1,2,3,4-tetrahydroisoquinolin-4-yl dimethyl carbamate Dimethyl carbamoyl chloride (0.54 g) was added dropwise to a mixture of (8-chloro-4-methoxy-3,4-dihydro-1H-isoqinoline-2-yl)-4-pyridinyl amine (1.5 g), triethylamine (2.1 g) and dimethylaminopyridine (0.10 g) in chloroform (56 mL), at ambient temperature. The reaction mixture was heated under reflux for 5 hrs, cooled and poured into saturated sodium bicarbonate solution. The layers were separated, and the aqueous phase was extracted with dichloromethane. The combined organic layers were washed with water and brine, dried over anhydrous magnesium sulfate, filtered, and the filtrate was concentrated. The residue was chromatographed on a Chromatotron, eluting with 2% triethylamine/23% methanol/75% ethyl acetate. The appropriate fractions were collected and concentrated to provide 0.64 g (44%) of product. Recrystallization from ethyl acetate gave (0.4 g) analytical sample (0.4 g), mp 193–194° C.

Analysis: Calculated for $C_{17}H_{19}ClN_4O_2$: 58.87% C 5.52% H 16.15% N Found: 58.73% C 5.47% H 16.17% N

EXAMPLE 59

5-Bromo-2-(pyridin-4-yl)amino-1,2,3,4-tetrahydroisoquinolin-8-ol

To a slurry of 5-bromo-8-methoxy-2-(4-pyridinylamino)-1,2,3,4-tetrahydroisoquinoline (2.9 g) in dichloromethane (25 ml) was cooled to –78° C., and boron tribromide (2.5 ml) was added. The reaction mixture was warmed to ambient temperature, stirred for 1.5 hrs, cooled to –78° C., and methanol (50 ml) was added. The mixture was evaporated to dryness in vacuo, and the residue was triturated with methanol/ethyl ether. The solid was collected to yield product 2.1 g (60.3%) as the hydrobromide salt. The mother liquors were basified with aqueous sodium hydrogen carbonate and extracted into 4:1 chloroform/2-propanol. The layers were separated, and the organic layer was concentrated. The residue was chromatographed over silica gel, eluting with 1% triethylamine, 5% methanol, 94% ethyl acetate; ending with 1% triethylamine, 20% methanol, 79% ethyl acetate. The appropriate fractions were collected and concentrated to yield 0.8 g (26%) of product. Trituration with methanol gave the analytical sample, mp 255–256° C.

Analysis: Calculated for $C_{14}H_{14}BrN_3O$: 52.52% C 4.41% H 13.12% N Found: 52.18% C 4.66% H 12.67% N

EXAMPLE 60

5-Bromo-2-(4-Pyridinylamino)-1,2,3,4-tetrahydroisoquinolin-8-yl dimethyl carbamate Dimethyl carbamoyl chloride (0.66 ml) was added dropwise to a mixture of 5-bromo-2-(pyridin-4-yl)amino-1,2,3, 4-tetrahydro isoquinolin-8-ol (2.1 g) and triethylamine (5 ml) in chloroform (50 ml), at ambient temperature. The reaction mixture was heated under reflux for 0.5 hr, stirred at ambient temperature overnight, and sodium bicarbonate solution and chloroform were added. The layers were separated and the organic layer was washed with water and brine, dried over anhydrous magnesium sulfate, filtered, and the filtrate was concentrated. The residue was chromatographed on silica gel, eluting with 1% triethylamine, 5% methanol, 94% ethyl acetate to 1% triethylamine, 20% methanol, 79% ethyl acetate. The appropriate fractions were collected and evaporated to yield 0.7 g (34%) of product. Recrystallization from methanol gave the analytical sample, mp 182–183° C.

Analysis: Calculated for $C_{17}H_{19}BrN_4O_2$: 52.19% C 4.89% H 14.32% N Found: 52.19% C 4.67% H 14.15% N

EXAMPLE 61

(5-Benzyloxy-3,4-dihydro-8-methoxy-1H-isoquinolin-2-yl)-4-pyridinylamine

Lithium aluminum hydride (4.3 g) was added portionwise at 0° C. to a suspension of N-[2-(2-benzyloxy-5-methoxyphenyl)ethylidene]-N-pyridin-4-ylhydrazine (13.2 g) in tetrahydrofuran (330 mL). The reaction mixture was stirred overnight at ambient temperature, and sodium sulfate decahydrate was added. The mixture was filtered and the filtrate was concentrated. The residue was chromatographed on silica gel, eluting with 1% triethylamine/2% methanol/97% ethyl acetate and 1% triethylamine/5% methanol/94% ethyl acetate. The appropriate fractions were collected and concentrated to yield product 12.0 g of N-[2-(2-benzyloxy-5-methoxy(phenyl)ethyl]-N-pyridinyl-4-hydrazine. A solution of N-[2-(2-benzyloxy-5-methoxyphenyl)ethyl]-N-pyridinyl-4-hydrazine (12.0 g) and chloromethyl methyl ether (2.9 ml) in acetic acid (150 ml) was heated under reflux for 1 hr. The reaction mixture was cooled, poured onto ice, neutralized with saturated sodium bicarbonate solution and extracted with ethyl acetate. The combined organic extracts were washed with water and brine, dried over anhydrous magnesium sulfate, filtered, and the filtrate was concentrated. The residue was chromatographed eluting with 1% triethylamine/2% methanol/97% ethyl acetate to 1% triethylamine/4% methanol/95% ethyl acetate. The appropriate fractions were collected and evaporated to provide 5.8 g (46.4%) of product. Recrystallization from ethyl acetate gave the analytical sample, mp 151–152° C.

Analysis: Calculated for $C_{22}H_{23}N_3O_2$: 73.11% C 6.41% H 11.63% N Found: 72.84% C 6.38% H 11.57% N

EXAMPLE 62

5-Fluoro-2-(pyridin-4-ylamino)-1,2,3,4-tetrahydroisoquinolin-8-ol hydrobromide

To a solution of (5-fluoro-8-methoxy-3,4-dihydro-1H-isoquinolin-2-yl)-pyridin-4-yl-amine (4.82 g) and dichloromethane (100 ml) at −78° C., boron tribromide (5.5 ml) was added, with stirring. The reaction mixture was warmed to ambient temperature, stirred for 3 hrs, and methanol (100 ml) was added. The mixture was stirred for 1 hr and concentrated in vacuo. The residue was recrystallized from 2-propanol to yield 4.45 g (74%) of product, mp 266° C.

Analysis: Calculated for $C_{14}H_{15}BrFN_3O$: 49.43% C 4.44% H 12.35% N Found: 49.34% C 4.30% H 12.33% N

EXAMPLE 63

2-(4-Pyridinylamino)-2,3,4,5-tetrahydro-1H-Benzo[c]azepine-7,8-diol Hydrochloride To a solution of [7-methoxy-8-hydroxy-1,3,4,5-tetrahydrobenzo[c]azepine-2-yl]pyridin-4-ylamine hydrochloride (1.0 g) in dichloromethane (10 mL) was slowly added boron tribromide (2.32 g), at 0° C. The reaction mixture was allowed to warm to ambient temperature, stirred overnight, methanol was added, and the solution was concentrated in vacuo. The residue was washed with saturated sodium bicarbonate solution and filtered. The filtrate crystallized. The precipitate was collected, washed with hydrochloric acid, and recrystallized from ethyl acetate-methanol to afford 425 mg (45%) of product. Trituration with hot dichloromethane gave the analytical sample, mp 240° C. (decomp.).

Analysis: Calculated for $C_{15}H_{18}ClN_3O_2$: 58.54% C 5.89% H 13.65% N Found: 58.00% C 5.78% H 13.54% N

EXAMPLE 64

2-(4-Pyridinylamino)-1,2,3,4-tetrahydroisoquinolin-8-yl dimethyl carbamate fumarate 5-Bromo-2-(4-pyridinylamino)-1,2,3,4-tetrahydroisoquinolin-8-yl dimethyl carbamate (0.22 g) was dissolved in ethanol (10 ml) and slowly added to 10% palladium-on-carbon (0.022 g). The mixture was hydrogenated at 50 psi overnight in a parr shaker at ambient temperature. The reaction mixture was filtered through a pad of Celite, and the pad was washed with methanol. The filtrate was concentrated. The residue was basified with sodium hydrogen carbonate solution and extracted with ethyl acetate. The extracts were dried over anhydrous magnesium sulfate, filtered, and the filtrate was concentrated. The residue was chromatographed on a Chromatotron, eluting with 1% triethylamine/5% methanol/94% ethyl acetate. The appropriate fractions were collected and concentrated. The residue was dissolved in hot methanol, and fumaric acid, dissolved in methanol, was added. The mixture was concentrated to one-half of its original volume, and several drops of ethyl ether were added. The precipitate was collected and dried to give 0.12 g (69%) of product, mp 201–202° C.

Analysis: Calculated for $C_{21}H_{24}N_4O_6$: 58.87% C 5.65% H 13.08% N Found: 58.56% C 5.64% H 12.87% N

EXAMPLE 65

8-Methoxy-2-(4-pyridinylamino)-1,2,3,4-tetrahydroisoquinolin-5-ol hydrochloride (5-Benzyloxy-3,4-dihydro-8-methoxy-1H-isoquinolin-2-yl)-4-pyridinylamine (2.5 g) was dissolved in methanol (60 ml) and slowly added to 10% palladium-on-carbon (0.4 g). Cyclohexene (14.5 ml) was added, and the mixture was heated under reflux, under nitrogen, for 4 hrs. The reaction mixture was filtered through a pad of Celite, and the pad was washed with methanol. The filtrate was concentrated, and the residue was dissolved in a small amount of 2-propanol. Ethanolic hydrochloric acid was added until the solution was acidic. The precipitate was collected to yield product 0.32 g (15.1%) mp 274–276° C. (dec). The mother liquor was basified with sodium bicarbonate solution and extracted with 2-propanol/chloroform (1:4). The layers were separated, and the organic layer was washed with water and brine, dried over anhydrous magnesium sulfate, filtered, and the filtrate was concentrated. The residue was chromatographed on silica dioxide, eluting with 1% triethylamine, 5% methanol, 94% ethyl acetate to 1% triethylamine, 20% methanol, 79% ethyl acetate to yield 1.4 g (90% overall yield) of product.

Analysis: Calculated for $C_{15}H_{18}ClN_3O_2$: 58.54% C 5.89% H 13.65% N Found: 58.31% C 5.95% H 13.37% N

EXAMPLE 66

(7-Methoxy-3,4-dihydro-1H-isoquinolin-2-yl)-4-pyridinylamine

To a mixture of lithium aluminum hydride (1.42 g) and dry tetrahydrofuran (50 ml), under nitrogen 7-methoxy-2-(4-pyridinylamino)-4H-isoquinoline-1,3-dione hydrochloride hemihydrate (4.10 g) was added in portions, with rapid stirring, at ambient temperature. The reaction mixture was stirred at ambient temperature, under nitrogen, for 4 hrs, and sodium sulfate decahydrate was added in portions. The mixture was filtered through a bed of celite, the filter cake washed thoroughly with ethyl acetate, and the filtrate was concentrated in vacuo. The residue was chromatographed over silica gel, eluting with 7% methanol-dichloromethane followed by 185:14:1 dichloromethane:methanol:ammonium hydroxide. The appropriate fractions were collected and evaporated. Absolute ethanol was added to the residue, the precipitate was collected and dried under vacuum at 80° C. overnight to give 300 mg (9%) of product, mp 188–189° C.

Analysis: Calculated for $C_{15}H_{17}N_3O$: 70.56% C 6.71% H 16.46% N Found: 70.08% C 6.59% H 16.26% N

EXAMPLE 67

2,3-Dihydro-2-(4-pyridinylamino)- 1H-isoindol-4-yl dimethylylcarbamate

To a mixture of 2,3-dihydro-2-(4-pyridinylamino)-1H-isoindol-5-ol (1.20 g), triethylamine (1.18 g) and chloroform (10 ml), dimethylcarbamoyl chloride (681 mg) in chloroform (10 ml) was added dropwise, with stirring, under nitrogen, at ambient temperature. The reaction mixture was heated under reflux for 2 hrs, poured into dilute sodium bicarbonate solution and the layers were separated. The aqueous phase was extracted with chloroform, and the combined organic extracts were dried over anhydrous sodium sulfate, filtered, and the filtrate was evaporated in vacuo. The residue was chromatographed on silica, eluting with 10–15% methanol-dichloromethane. The appropriate fractions were collected and concentrated. The residue was chromatographed over silica, eluting with 7% methanol:dichloromethane followed by 185:14:1 dichloromethane:methanol:ammonium hydroxide. The appropriate fractions were collected and concentrated to give 1.15 g (73%) of product. Recrystallization from ethyl acetate gave 550 mg (35%) of product, (dried under vacuum at 80° C.) mp 134–135° C.

Analysis: Calculated for $C_{16}H_{18}N_4O_2$: 64.41% C 6.08% H 18.78% N Found: 64.08% C 6.00% H 18.53% N

EXAMPLE 68

2,3-Dihydro-5-fluoro-N-(4-pyridinyl)-1H-isoindol-2-amine hydrochloride ⅛ hydrate A mixture of 4-fluorophthalic anhydride (5.99 g), 4-pyridinylhydrazine hydrochloride (5.00 g), and glacial acetic (30 ml) acid was stirred under reflux, under nitrogen, for 4 hrs. The reaction mixture was evaporated, and the residue was azeotroped with heptane. The residue was dried in vacuo to give 4-fluoro-2-(4-pyridinylamino)-isoindol-1,3-dione. To a mixture of lithium aluminum hydride (3.91 g) and dry tetrahydrofuran (100 ml), 2,3-dihydro-5-fluoro-2-(4-pyridinylamino)isoindole-1,3-dione hydrochloride was added in portions with rapid stirring, under nitrogen, at ambient temperature. The reaction mixture was stirred under nitrogen, overnight, at ambient temperature, and sodium sulfate decahydrate was added in portions. The mixture was filtered through a bed of celite, the filter cake was washed with ethyl acetate and concentrated in vacuo. The residue was chromatographed over silica gel, eluting with 7% methanol-dichloromethane, followed by 185:14:1 dichloromethane:methanol:ammonium hydroxide. The appropriate fractions were collected and evaporated. The residue was dissolved in absolute ethanol, excess concentrated hydrochloric acid was added, and the mixture was evaporated. The residue was crystallized from absolute ethanol to give 550 mg (6%) of product, (dried under vacuum at 80° C. overnight), mp 235–240° C. (decomp).

Analysis: Calculated for $C_{13}H_{12}N_3 \cdot HCl \cdot \frac{1}{8}H_2O$: 58.27% C 4.98% H 15.68% N Found: 58.11% C 4.91% H 15.96% N

EXAMPLE 69

2,3-Dihydro-4-fluoro-5-methoxy-N-(4-pyridinyl)-1H-isoindol-2-amine

To a solution of 2-(3-fluoro-4-methoxyphenyl)-4,4-dimethyl-4,5-dihydrooxazole (34.0 g) in dry tetrahydrofuran (300 ml) sec-butyllithium (140 ml of a 1.3 M solution in cyclohexane) was added dropwise at −78° C. with stirring, under nitrogen. The reaction mixture was stirred 15 mins, and carbon dioxide was bubbled below the surface. The reaction was stirred for 1 hr and water added dropwise. The mixture was basified with 10% sodium hydroxide solution and extracted with ethyl acetate. The aqueous extract was cooled to 0° C. and an equal volume of concentrated hydrochloric acid was added dropwise. The solution was stirred, under reflux overnight, cooled and the solid collected. The solid was washed with cold water and dried in vacuo to give 26.6 g of 3-fluoro-4-methoxyphthalic acid. A mixture of 3-fluoro-4-methoxyphthalic acid (26.6 g ) in acetic anhydride (100 ml) was stirred, under reflux, under nitrogen, for 4 hrs. The reaction mixture was cooled to −60° C. and filtered. The solid was collected, washed with ether and dried in vacuo to give 19.9 g (67%) of 3-fluoro-4-methoxyphthalic anhydride, mp 128–130° C. A mixture of 3-fluoro-4-methoxyphthalic anhydride (10.0 g) and 4-hydrazinopyridine hydrochloride (7.42 g) in glacial acetic acid (50 ml) was stirred, under reflux, under nitrogen, for 4 hrs and stirred at ambient temperature overnight. The solid was collected, washed with ether and dried in vacuo at 80° C. overnight to give 10.6 g (64%) of 4-fluoro-5-methoxy-2-(4-pyridinylamino)isoindol-1,3-dione. To a mixture of lithium aluminum hydride (3.72 g) and dry tetrahydrofuran (100 ml), 4-fluoro-5-methoxy-2-(4-pyridinylamino) isoindole-1,3-dione hydrochloride (10.60 g) was added in portions with rapid stirring, under nitrogen, at ambient temperature. The reaction mixture was stirred at ambient temperature, under nitrogen, for 3 hrs, and sodium sulfate decahydrate was added in portions. The mixture was filtered through a bed of celite, the filter pad was washed with ethyl acetate, and the filtrate was concentrated in vacuo. The residue was chromatographed over silica gel, eluting with 7% methanol-dichloromethane followed by 185:14:1 dichloromethane:methanol:ammonium hydroxide. The residue was crystallized from absolute ethanol to give 3.2 g (8%) of product, (dried under vacuum at 80° C. overnight) mp 206–210° C.

Analysis: Calculated for $C_{14}H_{14}FN_3O$: 64.85% C 5.44% H 16.21% N Found: 64.61% C 5.30% H 16.18% N

EXAMPLE 70

2,3-Dihydro-2-(4-pyridinylamino)-1H-isoindol-5-yl 1,2,3,4-tetrahydroisoquinolin-2-ylcarbamate ¼ hydrate To a mixture of 2,3-dihydro-2-(4-pyridinylamino)-1H-isoindol-5-ol (1.50 g), triethylamine (1.47 g), and chloroform (15 ml), 1,2,3,4-tetrahydroisoquinolin-2-ylcarbamyl chloride (1.55 g) in chloroform (10 ml) was added dropwise with stirring, under nitrogen, at ambient temperature. The reaction mixture was stirred under reflux for 3 hrs, at ambient temperature overnight and poured into dilute sodium bicarbonate solution. The layers were separated. The aqueous phase was extracted with chloroform, and the combined organic extracts were dried over anhydrous sodium sulfate, filtered, and the filtrate was evaporated in vacuo. The residue was chromatographed on silica, eluting with 7% methanol-dichloromethane followed by 185:14:1 dichloromethane-methanol-ammonium hydroxide. The appropriate fractions were collected and evaporated. The residue was recrystallized from ethanol-toluene to give 800 mg (31%) of product, mp 162–163° C.

Analysis: Calculated for $C_{23}H_{22}N_4O_2 \cdot \frac{1}{4}H_2O$: 70.66% C 5.80% H 14.33% N Found: 70.63% C 5.36% H 14.17% N

EXAMPLE 71

2,3-Dihydro-4-fluoro-2-(-4-pyridinylamino)-1 H-isoindol-5-ol hydrobromide

A solution of 2,3-dihydro-4-fluoro-5-methoxy-N-(4-pyridinyl)-1H-isoindol-2-amine (3.25 g) in 48% hydrobromic acid (25 ml) was stirred, under reflux, for 5 hrs. The reaction mixture was diluted with water and stirred at ambient temperature overnight. The mixture was cooled to approximately 10° C. and filtered. The filter cake was washed with cold water and dried under vacuum at 80° C. to give 2.8 g (69%) of product. Recrystallization from water gave the analytical sample, mp. >250° C., dried at 80° C. under vacuum.

Analysis: Calculated for $C_{13}H_{13}BrFN_3O$: 47.87% C 4.02% H 12.88% N Found: 47.82% C 3.85% H 12.81% N

EXAMPLE 72

2-(4-Pyridinylamino)-1,2,3,4-tetrahydroisoquinolin-7-ol

A mixture of 7-benzyloxy-2-(4-pyridinylamino)-1,2,3,4-tetrahydroisoquinoline (5.68 g) and 5% palladium-on-carbon (1.1 g) in methanol (85 mL) was shaken on a parr hydrogenation apparatus at ambient temperature, starting at an initial pressure of 55 psi. After 2 hrs an additional 1.1 g of catalyst was added, the pressure was increased to 55 psi, and the mixture was shaken for an additional 5 hrs. An additional 0.75 g of catalyst was added, the pressure was increased to 55 psi, and the mixture was shaken until hydrogen uptake ceased. The reaction mixture was filtered through a pad of Celite, and the pad was washed with methanol. Concentration of the filtrate gave 3.4 g (82%) of product. Recrystallization from ethanol gave the analytical sample, mp 236–239° C. (dec).

Analysis: Calculated for $C_{14}H_{15}N_3O$: 69.69% C 6.27% H 17.41% N Found: 69.37% C 6.18% H 17.16% N

EXAMPLE 73

8-Chloro-2-(4-pyridinylamino)-1,2,3,4-tetrahydroisoquinolin-5-ol hydrobromide

Boron tribromide (12.7 g) was added dropwise to a solution of (8-chloro-5-methoxy-3,4-dichloro-1H-isoquinoline-2-yl)-4-pyridinylamino (4.46 g) in dichloromethane (155 mL) at −78° C. The reaction mixture was stirred at ambient temperature for 3 hrs. The mixture was cooled to −78° C., and methanol (100 mL) was added. The mixture was stirred at ambient temperature for 1 hr and concentrated in vacuo. The residue was washed with methanol/ethyl ether to provide 4.6 g of product. A sample (2.5 g) was recrystallized from methanol to give 0.86 g (34%) of the analytical sample of the product, mp>260° C.

Analysis: Calculated for $C_{14}H_{15}BrClN_3O$: 47.15% C 4.24% H 11.78% N Found: 46.76% C 4.06% H 11.46% N

EXAMPLE 74

(5-Methoxy-3,4-dihydro-1H-isoquinolin-2-yl)-4-pyridinylamine dihydrochloride

Lithium aluminum hydride (4.9 g) was added portionwise to a suspension of N-[2-(2-methoxyphenyl)ethylidine]-N-pyridine-4-yl hydrazine hydrochloride (18.1 g) in tetrahydrofuran (325 mL), at 0° C. The reaction mixture was stirred at ambient temperature for 4 hrs, and sodium sulfate decahydrate was added. The mixture was filtered, and the filtrate was concentrated to provide 16.4 g of N-[2-(2-methoxyphenyl)ethyl]-N-pyridin-4-ylhydrazine. A solution of N-[2-(2-methoxyphenyl)ethyl]-N-pyridin-4-ylhydrazine (16.4 g) and chloromethyl methyl ether (5.76 g) in acetic acid (260 mL) was heated, under reflux, for 2 hrs, and the mixture was cooled to 0° C. Sodium hydroxide solution (50%) was added, and the mixture was extracted with ethyl acetate. The combined organic extracts were washed with water and brine, dried over anhydrous magnesium sulfate, filtered, and the filtrate was concentrated. The residue was chromatographed on silica, eluting with 10% methanol/ethyl acetate. The appropriate fractions were collected and concentrated to provide 9.4 g (57%) of product as the free base. The product free base was dissolved in methanol and ethereal hydrogen chloride was added. The precipitate was collected to give 1.0 g of product, mp 181–187° C. (dec).

Analysis: Calculated for $C_{15}H_{19}Cl_2N_3O$: 54.89% C 5.83% H 12.80% N Found: 54.90% C 5.78% H 12.75% N

EXAMPLE 75

(7-Benzyloxy-5-bromo-8-methoxy-3,4-dihydro-1H-isoquinolin-2-yl)-4-pyridinylamine hydrochloride Lithium aluminum hydride (5.4 g) was added portionwise at 0° C. to a suspension of N-[2-(4-benzyloxy-2-bromo-5-methoxyphenyl)ethylidene]-N-pyridin-4-ylhydrazine hydrochloride (26.0 g) in tetrahydrofuran (360 mL). The reaction mixture was stirred at ambient temperature for 3 hrs, and sodium sulfate decahydrate was added. The mixture was filtered, and the filtrate was concentrated to provide 24.3 g of N-[2-(4-benzyloxy-2-bromo-5-methoxyphenyl)ethyl]-N-pyridine-4-ylhydrazine. A solution of N-[2-(4-benzyloxy-2-bromo-5-methoxyphenyl)ethyl]-N-pyridine-4-yl hydrazine (24.3 g) and chloromethyl methyl ether (5.0 g) in acetic acid (225 mL) was heated under reflux for 2 hrs and cooled to 0° C. Sodium hydroxide solution (50%) was added and the mixture was extracted with ethyl acetate. The combined organic extracts were washed with water and brine, dried over anhydrous magnesium sulfate, filtered, and the filtrate was concentrated. The residue was triturated with ethyl acetate. The solid was collected and the filtrate was concentrated. The residue was chromatographed on silica, eluting with 10% methanol/ethyl acetate. The appropriate fractions were collected and concentrated to provide 8.1 g (33%) of product. The solid was dissolved in methanol and ethereal hydrogen chloride was added. The precipitate was collected to give the analytical sample, mp 235–237° C. (dec).

Analysis: Calculated for $C_{22}H_{23}ClBrN_3O_2$: 55.42% C 4.86% H 8.81% N Found: 55.32% C 4.74% H 8.64% N

EXAMPLE 76

N-[2-(3-Fluoro-4-methoxyphenyl)ethylidene]-N'-pyridin-4-yl-hydrazine hydrochloride A mixture of 2-fluoro-1-methoxy-4-(2-methoxyvinyl) benzene (20.0 g), 4-hydrazinopyridine (17.6 g), p-toluenesulfonic acid (1.0 g) and ethanol (mL) was heated under reflux for 6 hrs. The reaction mixture was cooled, filtered, and concentrated in vacuo. The residue was triturated with a mixture of methanol and ether. The solid was collected to give 18.1 g (55%) of product. Recrystallization from ethanol gave the analytical sample, mp 189–191° C.

Analysis: Calculated for $C_{14}H_{15}ClFN_3O$: 56.86% C 5.11% H 14.21% N Found: 56.79% C 4.96% H 14.14% N

EXAMPLE 77

2-(5-Chloro-2-methoxyphenyl)-4,4-dimethyl-4,5-dihydrooxazole

To a solution of 5-chloro-o-anisic acid (50 g) in toluene (100 mL) was added thionyl chloride (50 mL). The reaction mixture was heated under reflux for 2 hrs and distilled using a short path distillation apparatus to give 5-chloro-o-anisyl chloride, which was used in the next step. To a solution of 2-amino-2-methyl-1-propanol (38 mL) in dichloromethane (200 mL) was added a solution of 5-chloro-o-anisyl chloride in dichloromethane (150 mL) dropwise. The reaction mixture was stirred at ambient temperature for 1 hr, dichloromethane was added and the mixture was washed with 2 N hydrochloric acid. The organic phase was separated, dried over anhydrous magnesium sulfate, filtered, and the filtrate was concentrated in vacuo to give N-(2-(1-hydroxy-2-methylpropyl)-5-chloro-2-methoxy benzamide, which was used in the next step. To N-(2-(1-hydroxy-2-methylpropyl)-5-chloro-2-methoxy benzamide was added thionyl chloride (40 mL) at 0° C. The reaction mixture was stirred for 30 min, warmed to ambient temperature, diluted with diethyl ether (200 mL), and the mixture was stirred for 10 mins. The mixture was decanted, 10% sodium hydroxide solution was added, and the mixture was extracted with ethyl acetate. The organic extracts were combined, dried over anhydrous magnesium sulfate, filtered, and the filtrate was concentrated in vacuo to afford 41 g (64%) of product, mp 50–51° C.

Analysis: Calculated for $C_{12}H_{14}ClNO_2$: 60.13% C 5.89% H 5.84% N Found: 60.03% C 5.90% H 5.77% N

EXAMPLE 78

4-Chloro-7-methoxyisobenzofuran-1,3-dione

To a solution of 2-(5-chloro-2-methoxyphenyl)-4,4-dimethyl-4,5-dihydrooxazole (40.0 g) in tetrahydrofuran (250 mL) was added s-butyllithium (154 mL) at −78° C. The solution was stirred for 45 mins, and carbon dioxide was bubbled into the solution for 2 hrs. Water and ethyl acetate (500 mL) were added and the mixture was washed with 10% sodium hydroxide solution (500 mL). The aqueous phase was acidified with conc hydrochloric acid, and the mixture was heated under reflux for 12 hrs, cooled, and concentrated in vacuo to ⅓ the original volume. The precipitate was collected, washed with water and dried under vacuum to afford 3.43 g (10%) of product, mp 192–193° C.

Analysis: Calculated for $C_9H_5ClO_4$: 50.85% C 2.37% H Found: 50.85% C 2.22% H

EXAMPLE 79

2,3-Dihydro-4-chloro-7-methoxy-N-(4-pyridinyl)-1H-isoindol-2-amine

To a slurry of 4-chloro-7-methoxyisobenzofuran-1,3-dione (3.3 g) in acetic acid (25 mL) was added 4-hydrazinopyridine hydrochloride (2.25 g). The reaction mixture was heated under reflux for 3 hrs, cooled to 0° C., diluted with ethyl acetate and filtered. The filtrate was evaporated. The residue was dried to afford 4.24 g of 4-chloro-7-methoxyphthalimide. To a solution of 4-chloro-7-methoxyphthalimide (4.24 g) in tetrahydrofuran (50 mL) was added lithium aluminum hydride (1.38 g) in small portions, at ambient temperature. The reaction mixture was stirred for 3 hrs, and sodium sulfate decahydrate was added. The mixture was diluted with ethyl acetate (200 mL) and filtered. The filtrate was concentrated in vacuo and the residue was chromatographed over silica gel, eluting with dichloromethane:methanol (9:1). The appropriate fractions were collected and evaporated to afford 1.75 g of product, free base. The product free base was dissolved in a minimum amount of ethanol and conc hydrochloric acid was added. Ethyl acetate and heptane were added to afford 1.38 g of product, mp 229–230° C.

Analysis: Calculated for $C_{14}H_{15}Cl_2N_3O$: 53.86% C 4.84% H 13.46% N Found: 53.80% C 4.60% H 13.41% N

EXAMPLE 80

2,3-Dihydro-2-(4-pyridinylamino)-1H-isoindol-4-yl N-benzyl-N-methylcarbamate hydrochloride hemihydrate To a mixture of 2,3-dihydro-2-(4-pyridinylamino)-1H-isoindol-4-ol (1.50 g), triethylamine (1.47 g) and chloroform (15 ml), N-benzyl-N-methylcarbamyl chloride (1.55 g) in chloroform (10 ml) was added dropwise, with stirring, at ambient temperature, under nitrogen. The reaction mixture was stirred under reflux for 3 hrs, at ambient temperature overnight and poured into dilute sodium bicarbonate solution (100 ml). The layers were separated. The aqueous phase was extracted with chloroform and the combined organic layers were dried over anhydrous sodium sulfate, filtered, and the filtrate was evaporated in vacuo. The residue was chromatographed on silica, eluting with 7% methanol-dichloromethane followed by 185:14:1 methanol-dichloromethane-ammonium hydroxide. The appropriate fractions were collected and concentrated to give 1.35 g of product, free base. The product free base was dissolved in absolute ethanol and hydrogen chloride was added. Ether was added, and the mixture was cooled. The precipitate was collected to give 650 mg (23%) of product, mp 128–132° C.

Analysis: Calculated for $C_{22}H_{23}ClN_4O_2$: 62.93% C 5.76% H 13.34% N Found: 62.96% C 5.57% H 13.45% N

EXAMPLE 81

N-[2-(5-Benzyloxy-2-bromo-4-methoxyphenyl)ethylidene]-N'-pyridin-4-yl-hydrazine hydrochloride A mixture of 5-benzyloxy-2-bromo-4-methoxy-3-(2-methoxyvinyl)benzene (42.1 g), 4-hydrazinopyridine hydrochloride (19.0 g), p-toluenesulfonic acid (0.23 g) and ethanol (350 ml) was heated under reflux overnight, with stirring. The reaction mixture was cooled and filtered. Recrystallization of the precipitate from methanol yielded 40.2 g, (72.2%) of product, mp 232–233° C.

Analysis: Calculated for $C_{21}H_{21}BrClN_3O_2$: 54.50% C 4.57% H 9.08% N Found: 54.36% C 4.41% H 8.95% N

EXAMPLE 82

(3,4-Dihydro-8-benzyloxy-5-bromo-7-methoxy-1H-isoquinolin-2-yl)-4-pyridinylamine fumarate Lithium aluminum hydride (10.7 g) was added portionwise at 0° C. to a suspension of N-[2-(5-benzyloxy-2- bromo-4-methoxyphenyl)ethylidine]-N-pyridin-4-ylhydrazine hydrochloride (39.4 g) in tetrahydrofuran (1 L). The reaction mixture was stirred overnight at ambient temperature, and sodium sulfate decahydrate was added. The mixture was filtered and the filtrate was concentrated to provide (27.7 g) of N-[2-(5-benzyloxy-2-bromo-4-methoxyphenyl)ethyl]-N-pyridin-4-yl)hydrazine. A solution of N-[2-(5-benzyloxy-2-bromo-4-methoxyphenyl)ethyl]-N-pyridin-4-ylhydrazine (27.7 g) and chloromethyl methyl ether (5.4 ml) in acetic acid (400 ml) was heated under reflux for 1.5 hrs, under nitrogen. The reaction mixture was cooled and poured onto ice. 2 N Sodium hydroxide solution was added to neutrality, and the mixture was extracted with ethyl acetate. The combined organic extracts were washed with water and brine, dried over anhydrous magnesium sulfate, filtered, and the filtrate was concentrated. The residue was chromatographed on silica, eluting with 1% triethylamine/2% methanol/97% ethyl acetate 1% triethylamine/4% methanol/95% ethyl acetate. The appropriate fractions were collected and evaporated to provide 12.5 g of product (44% overall yield). The fumarate salt was prepared from methanol and fumaric acid and had mp 186–187° C.

Analysis: Calculated for $C_{26}H_{26}BrN_3O_6$: 56.12% C 4.71% H 7.55% N Found: 55.78% C 4.23% H 7.29% N

EXAMPLE 83

7-Methoxy-2-(4-pyridinylamino)-1,2,3,4-tetrahydroisoquinolin-8-ol hydrobromide (8-Benzyloxy-5-bromo-3,4-dihydro-7-methoxy-1H-isoquinolin-2-yl)-4-pyridinylamine) (11 g) was dissolved in ethanol (250 ml) and slowly added to 5% palladium-on-carbon (2.2 g). The mixture was hydrogenated at 55 psi overnight in a parr shaker at ambient temperature. The reaction mixture was filtered through a pad of Celite, and the pad was washed well with methanol. The filtrate was concentrated, and the precipitate was collected and dried to give 8.3 g, 94.6% of product, mp 235–236° C.

Analysis: Calculated for $C_{15}H_{18}BrN_3O_2$: 51.15% C 5.15% H 11.93% N Found: 51.07% C 4.93% H 11.82% N

EXAMPLE 84

7-Methoxy-2-(4-pyridinylamino)-1,2,3,4-tetrahydroisoquinolin-8-yl dimethyl carbamate fumarate Dimethyl carbamoyl chloride (0.6 ml) was added dropwise to a mixture of 7-methoxy-2-(4-pyridinylamino)-1,2,3,4-tetrahydroisoquinoline-8-ol) hydrobromide (1.5 g) and triethylamine (2.5 ml) in chloroform (75 ml) at ambient temperature. The reaction mixture was heated under reflux overnight, cooled, and diluted with sodium bicarbonate solution and chloroform. The layers were separated and the organic layer was washed with water and brine, dried over anhydrous magnesium sulfate, filtered, and the filtrate was concentrated. The residue was chromatographed on silica, eluting with 1% triethylamine, 5% methanol, 94% ethyl acetate to 1% triethylamine, 20% methanol, 79% ethyl acetate. The appropriate fractions were collected and concentrated to yield 1.1 g (75%) of product. The fumarate was prepared from fumaric acid and methanol and had mp 176–177° C.

Analysis: Calculated for $C_{22}H_{26}N_4O_7$: 57.64% C 5.72% H 12.22% N Found: 57.53% C 5.72% H 12.04% N

EXAMPLE 85

2,3-Dihydro-2-(4-pyridinylamino)-1H-isoindol-4-yl diethylcarbamate hydrochloride To a mixture of 2,3-dihydro-2-(4-pyridinylamino)-1H-isoindol-4-ol (1.50 g), triethylamine (1.47 g) and chloroform (15 ml), diethylcarbamyl chloride (1.07 g) in chloroform (10 ml) was added dropwise, with stirring at ambient temperature, under nitrogen. The reaction mixture was stirred under reflux for 5 hrs, at ambient temperature overnight, and poured into dilute sodium bicarbonate solution (100 ml). The layers were separated. The aqueous phase was extracted with chloroform, and the combined organic layers were dried over anhydrous magnesium sulfate, filtered, and the filtrate was evaporated in vacuo. The residue was flash chromatographed (silica), eluting with 7% methanol-dichloromethane followed by 185:14:1 dichloromethane-methanol-ammonium hydroxide. The appropriate fractions were collected and evaporated. The residue was dissolved in absolute ethanol and treated with excess ethereal hydrogen chloride. The precipitate was recrystallized from ethanol-ether to give 1.20 g (50%) of product, mp 213–215° C. (dec).

Analysis: Calculated for $C_{18}H_{23}ClN_4O_2$: 59.58% C 6.39% H 15.44% N Found: 59.48% C 6.47% H 15.06% N

EXAMPLE 86

2,3-Dihydro-4-fluoro-2-(4-pyridinylamino)-1H-isoindol-5-yl dimethylcarbamate hydrochloride To a mixture of 2,3-dihydro-4-fluoro-2-(4-pyridinylamino)-1H-isoindol-5-ol hydrobromide (600 mg), triethylamine (614 mg), and chloroform (10 ml), dimethylcarbamyl chloride (237 mg) in chloroform (5 ml) was added dropwise, with stirring at ambient temperature, under nitrogen. The reaction mixture was stirred under reflux for 5 hrs, at ambient temperature overnight and poured into dilute sodium bicarbonate solution (100 ml). The layers were separated. The aqueous phase was extracted with chloroform, and the combined organic layers were dried over anhydrous magnesium sulfate, filtered, and the filtrate was evaporated in vacuo. The residue was flash chromatographed (silica), eluting with 7% methanol-dichloromethane followed by 185:14:1 dichloromethane-methanol-ammonium hydroxide. The appropriate fractions were collected and evaporated. The residue was dissolved in absolute ethanol and excess ethereal hydrogen chloride was added. Ether was added and the solution was cooled. The precipitate was collected to give 450 mg (69%) of product, mp 250–252° C. (dec).

Analysis: Calculated for $C_{16}H_{18}ClFN_4O_2$: 54.47% C 5.14% H 15.88% N Found: 54.30% C 5.08% H 15.60% N

EXAMPLE 87

2,3-Dihydro-4-chloro-2-(4-pyridinylamino)-1H-isoindol-7-ol dihydrobromide

To a solution of 2,3-dihydro-4-chloro-7-methoxy-N-(4-pyridinyl)-1H-isoindol-2-amine hydrochloride (1.12 g) in dichloromethane (10 mL) was added boron tribromide (1.0 mL) at 0° C. The solution was warmed to ambient temperature and stirred for 3 days. Methanol was added, and the mixture was filtered to give 1.2 g (79%) of product, mp>240° C. (decomp).

Analysis: Calculated for $C_{13}H_{14}ClBr_2N_3O$: 36.87% C 3.33% H 9.92% N Found: 36.29% C 3.15% H 9.70% N

EXAMPLE 88

2,3-Dihydro-4-fluoro-2-(4-pyridinylamino)-1H-isoindol-5-yl 1,2,3,4-tetrahydroisoquinolin-2-ylcarbamate hydrochloride To a mixture of 2,3-dihydro-4-fluoro-2-(4-pyridinylamino)-1H-isoindol-5-ol hydrobromide (655 mg), triethylamine (671 mg), and chloroform (10 ml), 1,2,3,4-tetrahydroisoquinolin-2-ylcarbonyl chloride (471 mg) in chloroform (5 ml) was added dropwise, with stirring at ambient temperature, under nitrogen. The reaction mixture was stirred under reflux for 5 hrs, at ambient temperature overnight and poured into dilute sodium bicarbonate solution (100 ml). The layers were separated. The aqueous phase was extracted with chloroform, and the combined organic layers were dried over anhydrous sodium sulfate, filtered, and the filtrate was evaporated in vacuo. The residue was flash chromatographed (silica), eluting with 7% methanol-dichloromethane followed by 185:14:1 dichloromethane-methanol-ammonium hydroxide to give 800 mg of product. The appropriate fractions were collected and evaporated. The residue was dissolved in absolute ethanol and excess ethereal hydrogen chloride was added. Ether was added and the mixture was cooled. The precipitate was collected to give 750 mg (85%) of product, mp >260° C.

Analysis: Calculated for $C_{23}H_{22}FN_4O_2$: 62.66% C 5.03% H 12.71% N Found: 62.22% C 4.99% H 12.59% N

EXAMPLE 89

2-(4-pyridinylamino)-1,2,3,4-tetrahydro-isoquinolin-5-ol hydrobromide monohydrate Boron tribromide (22.6 g) was added dropwise to a solution of 4-methoxy-3,4-dihydro-1H-isoquinoline-2-yl-4-pyridinylamine (7.0 g) in dichloromethane (275 mL) at –78° C. The dry ice bath was removed, and the suspension was stirred at ambient temperature for 3 hrs. The reaction mixture was cooled to –78° C., methanol (150 mL) was added, and the mixture was stirred at ambient temperature for 1 hr and concentrated in vacuo. The residue was washed with methanol/ethyl ether to provide 8.4 g (95%) of product. Recrystallization from 2-propanol gave the analytical sample, mp 248–252° C. (dec).

Analysis: Calculated for $C_{14}H_{18}BrN_3O_2$: 49.42% C 5.33% H 12.35% N Found: 49.16% C 4.96% H 12.10% N

EXAMPLE 90

3,4-Dihydro-1H-isoquinolin-2-carboxylicacid-7-methoxy-2-(4-pyridinylamino)-2,3,4,5-t etrahydro-1H-benzo[c]azepin-8-yl ester hydrochloride To a solution of [7-methoxy-8-hydroxy-1,3,4,5-tetrahydro-benzo[c]azepin-2-yl]-pyridin-4-yl amine hydrochloride (500 mg) in chloroform (10 mL) was added 1,2,3,4-tetrahydroisoquinoline-2-yl carbonyl chloride (362 mg) followed by triethylamine (0.75 mL). The reaction mixture was heated under reflux for 3 hrs, cooled to ambient temperature, diluted with dichloromethane (200 mL), and the mixture was washed with saturated sodium bicarbonate solution. The organic phase was separated, dried under anhydrous magnesium sulfate, filtered, and the filtrate was concentrated in vacuo. The residue was flash chromatographed over silica gel, eluting with chloroform:methanol (9:1). The appropriate fractions were collected and evaporated. The residue was dissolved in methanol and conc hydrochloric acid was added. The precipitate was collected and crystallized from ethyl acetate-petroleum ether to give 230 mg of product, mp >100° C. (dec).

Analysis: Calculated for $C_{26}H_{29}ClN_4O_3$: 64.93% C 6.08% H 11.65% N Found: 64.48% C 6.02% H 11.21% N

EXAMPLE 91

2,3-Dihydro-4-chloro-2-(4-pyridylamino)-1H-isoindol-7-yl dimethyl carbamate hydrochloride To a solution of 2,3-dihydro-4-chloro-2-(4-pyridinylamino)-1H-isoindol-7-ol dihydrobromide (600 mg) in chloroform (10 ml), dimethylcarbamyl chloride (156 mL) followed by triethylamine (0.68 mL) was added. The reaction mixture was heated under reflux for 4 hrs, cooled to ambient temperature and stirred for two days. Dichloromethane (100 mL) was added and the solution was washed with saturated sodium bicarbonate solution. The organic phase was separated, dried over anhydrous magnesium sulfate, filtered, and the filtrate was concentrated in vacuo. The residue was flash chromatographed over silica gel, eluting with 10% methanol in dichloromethane. The residue was dissolved in methanol and conc hydrochloric acid was added. The mixture was concentrated in vacuo, the precipitate was collected and recrystallized from dichloromethane-methanol to give 285 mg (54%) of product, >200° C. (dec).

Analysis: Calculated for $C_{16}H_{17}ClN_4O_2$ HCl: 52.05% C 4.91% H 15.17% N Found: 51.88% C 4.59% H 15.04% N

EXAMPLE 92

2,3-Dihydro-2-(4-pyridinylamino)-1H-isoindol-4-yl4-(2-pyridinyl)-1-piperazinyl-carbamate ¼ hydrate To a mixture of 2,3-dihydro-2-(4-pyridinylamino)-1H-isoindol-4-ol (1.50 g), triethylamine (1.47 g) and chloroform (15 ml), 4-(2-pyridinyl)-1-piperazinylcarbonyl chloride (1.79 g) in chloroform (10 ml) was added dropwise, with stirring at ambient temperature, under nitrogen. The reaction mixture was heated under reflux for 3 hrs, stirred at ambient temperature, under nitrogen, overnight and poured into dilute sodium bicarbonate solution. The layers were separated. The aqueous phase was extracted with chloroform, and the combined organic layers were dried over anhydrous sodium sulfate, filtered, and the filtrate was evaporated in vacuo. The residue was flash chromatographed on silica, 185:14:1 dichloromethane:methanol:ammonium hydroxide. The appropriate fractions were collected and evaporated. The residue was chromatographed (silica), eluting with 192:7:1 ethyl acetate:methanol:ammonium hydroxide. The appropriate fractions were collected and evaporated to give 450 mg (16%) of product. Recrystallization from ethyl acetate-ether gave the analytical sample, mp 98–101° C.

Analysis: Calculated for $C_{23}H_{24}N_6O_2 \cdot \frac{1}{4}H_2O$: 65.62% C 5.87% H 19.96% N Found: 65.70% C 5.49% H 20.07% N REACTION SCHEME A
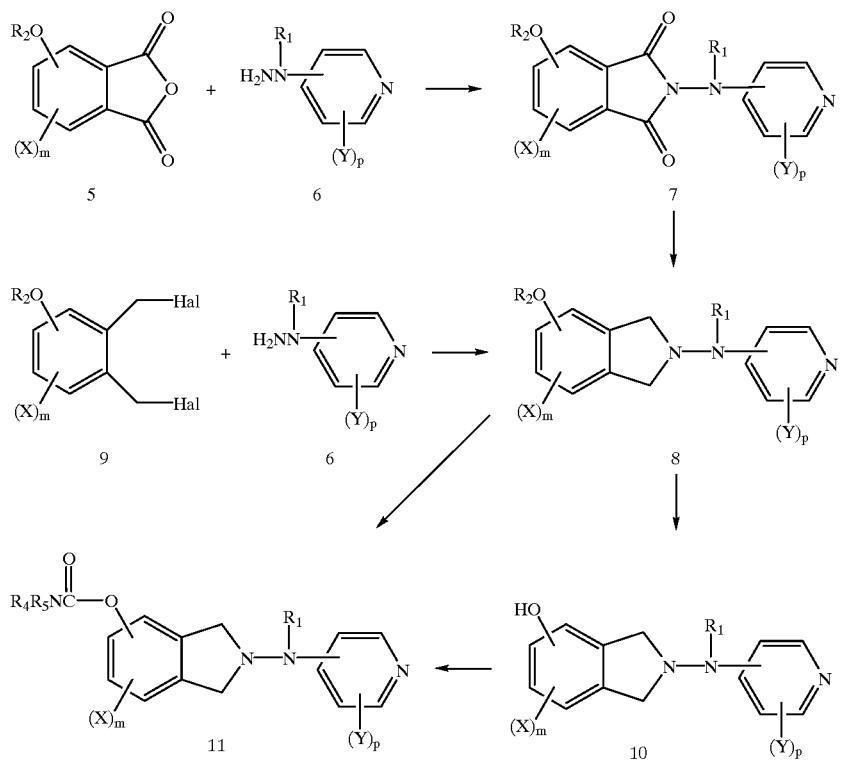
REACTION SCHEME B
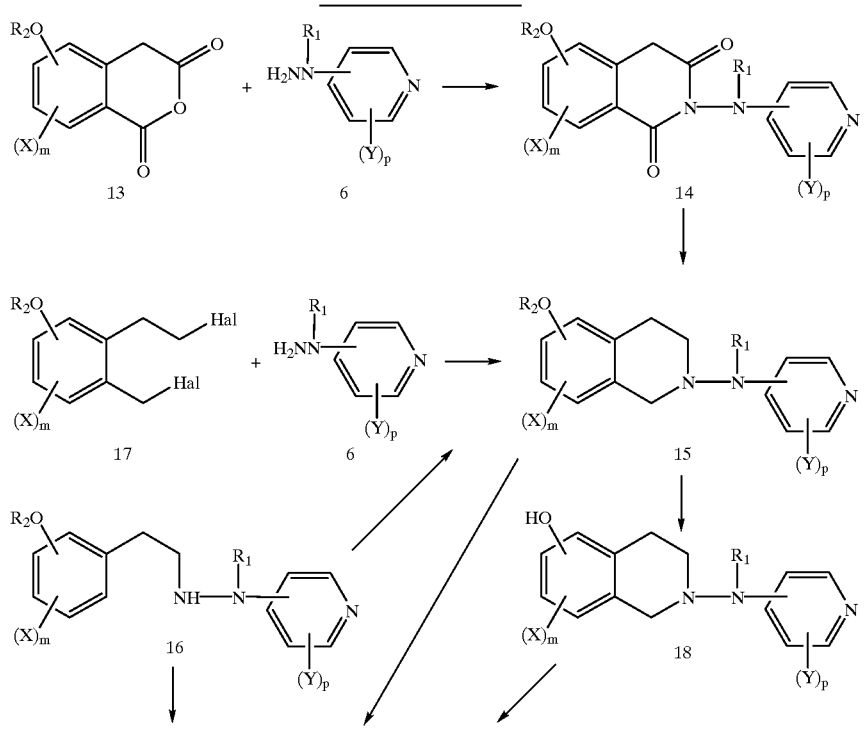

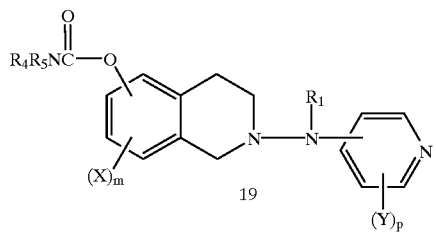
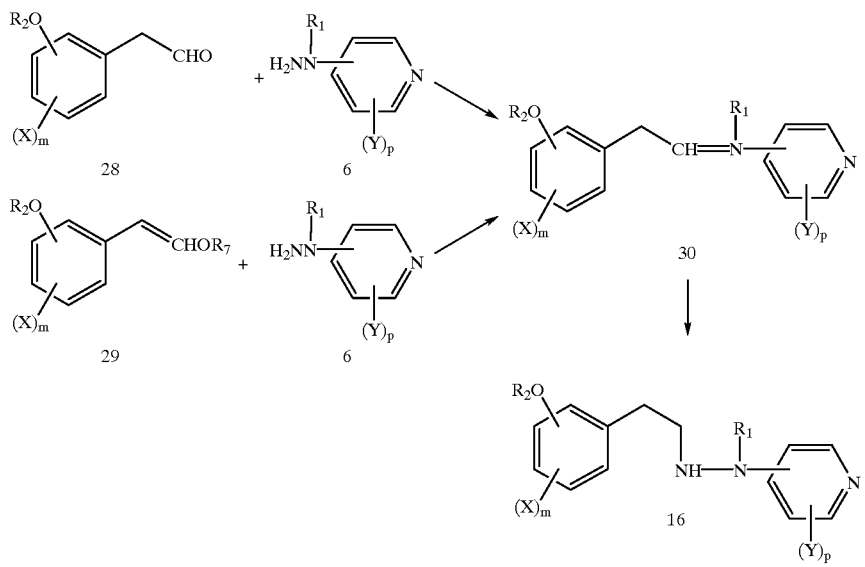
wherein $R_1$, $R_2$, $R_4$, $R_5$, $R_7$, X, Y, m and P are as herein described.
REACTION SCHEME C
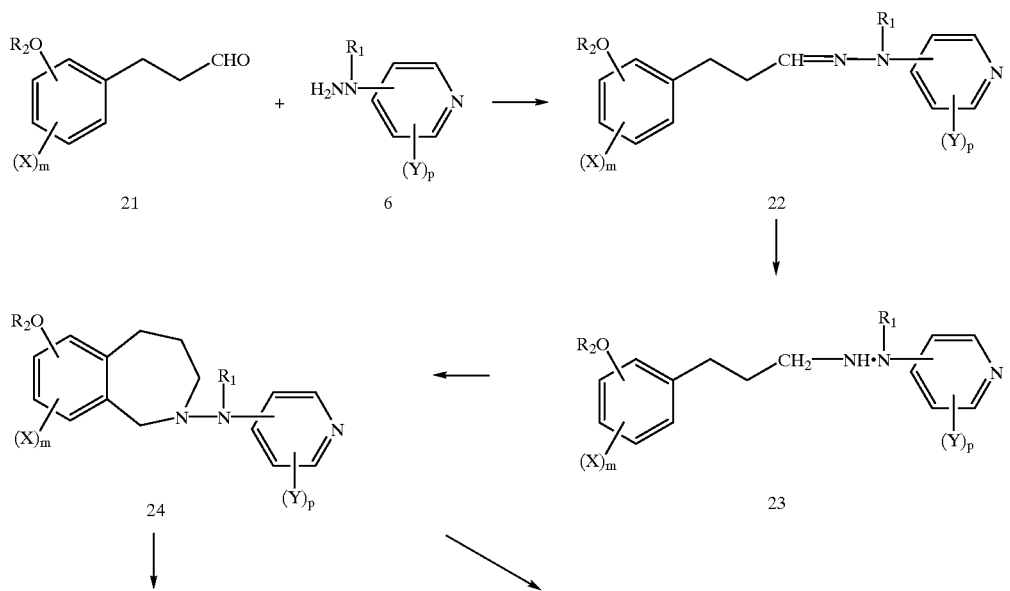

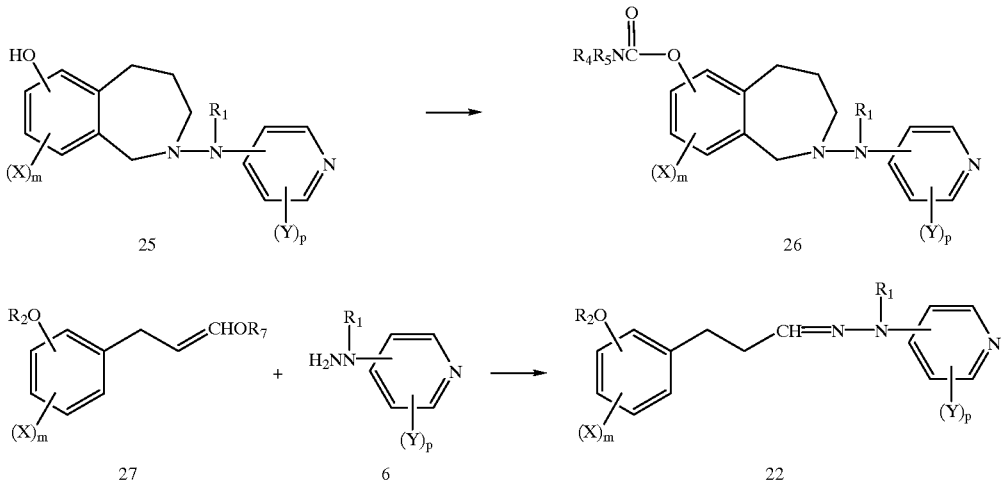

wherein $R_1$, $R_2$, $R_4$, $R_5$, $R_7$, X, Y, m and P are as herein described.

What is claimed is:

1. A compound of the formula

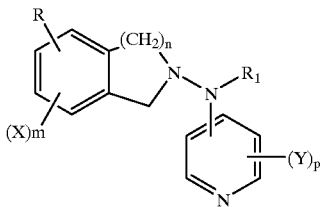

wherein R is hydrogen, a group of the formula $R_2O$— wherein $R_2$ is hydrogen, loweralkyl, benzyl, a group of the formula $(R_3)_3Si$— wherein $R_3$ is loweralkyl, or a group of the formula $R_4R_5NCO$— wherein $R_4$ and $R_5$ are independently hydrogen, loweralkyl or benzyl; $R_4$ and $R_5$ taken together with the nitrogen atom to which they are attached form a group of the formula

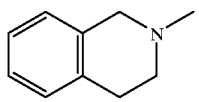

or a group of the formula

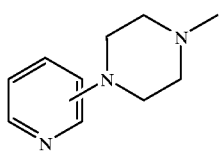

$R_1$ is hydrogen or loweralkyl; X is hydrogen, loweralkyl, halogen, hydroxy, loweralkoxy, or trifluoromethyl; Y is hydrogen, loweralkyl, halogen, hydroxy, loweralkoxy, or trifluoromethyl; m is 1 or 2; n is 1, 2, or 3; p is 1 or 2; the optical isomers thereof; or the pharmaceutically acceptable salts thereof.

2. A compound according to claim 1 wherein R is a group of the formula $R_2O$— wherein $R_2$ is a group of the formula $R_4R_5NCO$—.

3. A compound according to claim 2 which is selected from the group consisting of;
2,3-dihydro-2-[(N-2-pyridinyl)amino]-1H-isoindol-5-yl methyl carbamate;
2,3-dihydro-2-[(N-2-pyridinyl)amino]-1H-isoindol-4-yl methyl carbamate, 2,3-dihydro-2-(4-pyridinylamino)-1H-isoindol-4-yl dimethylcarbamate;
6-methoxy-2-(4-pyridinylamino)-1,2,3,4-tetrahydroisoquinolin-7-yl dimethylcarbamate;
2-(4-pyridinylamino)-1,2,3,4-tetrahydroisoquinolin-6-yl dimethyl carbamate;
2-(4-pyridinylamino)-1,2,3,4-tetrahydroisoquinolin-7-yl dimethyl carbamate;
7-methoxy-2(4-pyridinylamino)-1,2,3,4-tetrahydroisoquinolin-6-yl dimethyl carbamate;
dimethylcarbamic acid 2-((4-pyridinylamino)-2,3,4,5-tetrahydro-1H-benzo[c]azepin-7-yl ester hydrochloride 0.25 hydrate;
dimethylcarbamic acid 7-methoxy-2-(4-pyridinylamino)-2,3,4,5-tetrahydro-1H-benzo[c]azepin-8-yl ester;
2,3-dihydro-2-(4-pyridinylamino)-1H-isoindol-4-yl-1,2,3,4-tetrahydroisoquinolin-2-yl carbamate; and
2,3-dihydro-5-[[tris(1-methylethyl)silyl]oxy]-N-2-pyridinyl-1H-isoindol-2-amine.

4. A compound according to claim 1 which is selected from the group consisting of;
[7-methoxy-8-tert-butyldimethylsilyloxy-1,3,4,5-tetrahydrobenzo[c]azepin-2-yl]pyridine-4-yl amine;
2,3-dihydro-N-2-pyridinyl-1H-isoindol-2-amine;
3,4-dihydro-N-2-pyridinyl-2(1H)-isoquinolinamine;
2,3-dihydro-2-[(N-2-pyridinyl)amino]-1H-isoindol-5-ol;
2,3-dihydro-4-methoxy-N-2-pyridinyl-2H-isoindol-2-amine;
2,3-dihydro-2-[N-2-pyridinyl)amino]-1H-isoindol-7-ol;
3,4-dihydro-N-4-pyridinyl-2(1H)-isoquinolinamine;
2,3-dihydro-N-4-pyridinyl-1H-isoindol-2-amine;
4-bromo-2,3-dihydro-N-4-pyridinyl-1H-isoindol-2-amine;
2,3-dihydro-4-methoxy-N-(pyridinyl)-1H-isoindol-2-amine;
2,3-dihydro-N-methyl-N-(4-pyridinyl)-1H-isoindol-2-amine;
2,3-dihydro-2-(4-pyridinylamino)-1H-isoindol-4-ol;
(7-methoxy-1,3,4,5-tetrahydro-2-benzo[c]azepinyl)-4-pyridinylamine;
7-methoxy-2-(pyridin-4-yl amino)-1,2,3,4-tetrahydroisoquinolin-6-ol;

(3,4-dihydro-6-methoxy-1H-isoquinolin-2-yl)-4-pyridinylamine;
(7-methoxy-1,3,4,5-tetrahydro-benzo[c]azepin-4-yl)-methyl-1-pyridin-4-yl-amine;
7-benzyloxy-3,4-dihydro-1H-isoquinolin-2-yl)-4-pyridinylamine;
[7-methoxy-8-hydroxy-1,3,4,5-tetrahydrobenzo[c]azepine-2-yl]pyridin-4-ylamine;
(2,3-dihydro-(1H)-isoindol-2-yl)-(3-fluoro-pyridin-4-yl) amine;
2,3-dihydro-5-methoxy-N-(4-pyridinyl)-1H-isoindol-2-amine;
2,3-dihydro-2-(4-pyridinylamino)-1H-isoindol-5-ol;
2-[methyl-(pyridin-4-yl)amino]-1,2,3,4-tetrahydro-isoquinolin-6-ol;
(6-fluoro-7-methoxy-3,4-dihydro-1H-isoquinolin-2-yl)-4-pyridinylamine;
(5-bromo-3,4-dihydro-8-methoxy-1H-isoquinolin-2-yl)-4-pyridinylamine; and
(3,4-dihydro-8-methoxy-1H-isoquinolin-2-yl)-4-pyridinylamine.

5. A process for the preparation of a compound of the formula

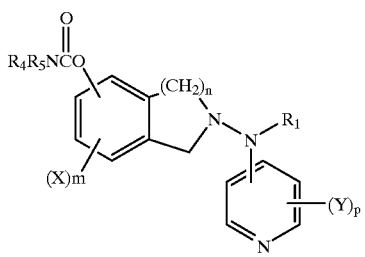

wherein $R_1$ is hydrogen or loweralkyl; $R_4$ and $R_5$ are independently hydrogen or loweralkyl; $R_4$ and $R_5$ taken together with the nitrogen atom to which they are attached form a group of the formula

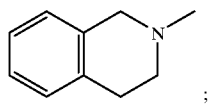

X is hydrogen, loweralkyl, halogen, hydroxy, loweralkoxy, or trifluoromethyl; Y is hydrogen, loweralkyl, halogen, hydroxy, , or trifluoromethyl; m is 1 or 2; n is 1, 2, or 3; and p is 1 or 2, which process comprises contacting a compound of the formula

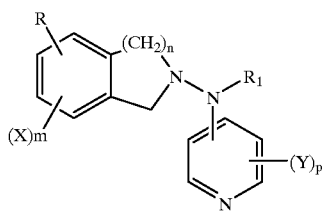

wherein R is hydroxyl and $R_1$, X, Y, m, n, and p are as herein defined with a compound of the formula

wherein $R_4$ and $R_5$ are as herein defined and Hal is chloro or bromo.

6. The process of claim 5 wherein a solvent is employed.
7. The process of claim 6 wherein the solvent is a halocarbon.
8. The process of claim 7 wherein the halocarbon is chloroform.
9. The process of claim 5 wherein an acid acceptor is employed.
10. The process of claim 9 wherein the acid acceptor is a tertiary amine.
11. The process of claim 10 wherein the tertiary amine is triethylamine.
12. A process for the preparation of a compound of the formula

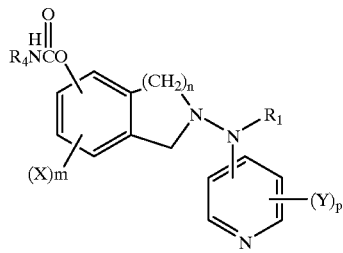

wherein $R_1$ is hydrogen or loweralkyl; $R_4$ is hydrogen or loweralkyl; X is hydrogen, loweralkyl, halogen, hydroxy, loweralkoxy, or trifluoromethyl; Y is hydrogen, loweralkyl, halogen, hydroxy, loweralkoxy, or trifluoromethyl; m is 1 or 2; n is 1, 2, or 3; and p is 1 or 2 which comprises contacting a compound of the formula

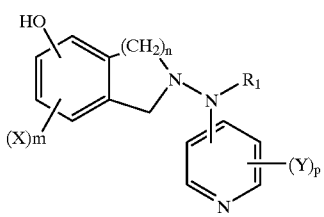

wherein $R_1$, X, Y, m, n, and p are as herein defined with a compound of the formula

wherein $R_4$ is as herein defined.

13. The process of claim 12 wherein a solvent is employed.
14. The process of claim 13 wherein the solvent is acetonitrile.
15. The process of claim 12 wherein a base is employed.
16. The process of claim 15 wherein the base is 1,8-diazabicyclo[5.4.0]undec-7-ene.
17. A compound according to claim 1 which is selected from the group consisting of;
6-fluoro-2-(4-pyridinylamino)-1,2,3,4-tetrahydroisoquinolin-7-ol;
6-fluoro-2-(4-pyridinylamino)-1,2,3,4-tetrahydroisoquinolin-7-yl dimethyl carbamate;

(8-chloro-5-methoxy-3,4-dihydro-1H-isoquinolin-2-yl)-4-pyridinylamine;
8-chloro-2-(4-pyridinylamino)-1,2,3,4-tetrahydroisoquinolin-5-yl dimethyl carbamate;
5-bromo-2-(pyridin-4-yl)amino-1,2,3,4-tetrahydroisoquinolin-8-ol;
5-bromo-2-(4-pyridinylamino)-1,2,3,4-tetrahydroisoquinolin-8-yl dimethyl carbamate;
(5-benzyloxy-3,4-dihydro-8-methoxy-1H-isoquinolin-2-yl)-4-pyridinylamine;
5-fluoro-2-(pyridin-4-ylamino)-1,2,3,4-tetrahydroisoquinolin-8-ol;
2-(4-pyridinylamino)-2,3,4,5-tetrahydro-1H-benzo[c]azepine-7,8-diol;
2-(4-pyridinylamino)-1,2,3,4-tetrahydroisoquinolin-8-yl dimethyl carbamate;
8-methoxy-2-(4-pyridinylamino)-1,2,3,4-tetrahydroisoquinolin-5-ol;
(7-methoxy-3,4-dihydro-1H-isoquinolin-2-yl)-4-pyridinylamine;
2,3-dihydro-2-(4-pyridinylamino)-1H-isoindol-4-yl dimethylcarbamate;
2,3-dihydro-5-fluoro-N-(4-pyridinyl)-1H-isoindol-2-amine;
2,3-dihydro-4-fluoro-5-methoxy-N-(4-pyridinyl)-1H-isoindol-2-amine;
2,3-dihydro-2-(4-pyridinylamino)-1H-isoindol-5-yl 1,2,3,4-tetrahydroisoquinolin-2-ylcarbamate;2,3-dihydro-4-fluoro-2-(4-pyridinylamino)-1H-isoindol-5-ol;
2-(4-pyridinylamino)-1,2,3,4-tetrahydroisoquinolin-7-ol;
8-chloro-2-(4-pyridinylamino)-1,2,3,4-tetrahydroisoquinolin-5-ol;
(4-methoxy-3,4-dihydro-1H-isoquinolin-2-yl)-4-pyridinylamine;
(7-benzyloxy-5-bromo-8-methoxy-3,4-dihydro-1H-isoquinolin-2-yl)-4-pyridinylamine;
2,3-dihydro-4-chloro-7-methoxy-N-(4-pyridinyl)-1H-isoindol-2-amine;
2,3-dihydro-2-(4-pyridinylamino)-1H-isoindol-4-yl N-benzyl-N-methylcarbamate;
(3,4-dihydro-8-benzyloxy-5-bromo-7-methoxy-1H-isoquinolin-2-yl)-4-pyridinylamine;
7-methoxy-2-(4-pyridinylamino)-1,2,3,4-tetrahydroisoquinolin-8-ol;
7-methoxy-2-(4-pyridinylamino)-1,2,3,4-tetrahydroisoquinolin-8-yl dimethyl carbamate;
2,3-dihydro-2-(4-pyridinylamino)-1H-isoindol-4-yl diethylcarbamate;
2,3-dihydro-4-fluoro-2-(4-pyridinylamino)-1H-isoindol-5-yl dimethylcarbamate;
2,3-dihydro-4-chloro-2-(4-pyridinylamino)-1H-isoindol-7-ol;
2,3-dihydro-4-fluoro-2-(4-pyridinylamino)-1H-isoindol-5-yl 1,2,3,4-tetrahydroisoquinolin-2-ylcarbamate;
2-(4-pyridinylamino)-1,2,3,4-tetrahydroisoquinolin-5-ol;
3,4-dihydro-1H-isoquinolin-2-carboxylic acid-7-methoxy-2-(4-pyridinylamino)-2,3,4,5-tetrahydro-1H-benzo[c]azepin-8-yl ester;
2,3-dihydro-4-chloro-2-(4-pyridylamino)-1H-isoindol-7-yl dimethyl carbamate;
2,3-dihydro-2-(4-pyridinylamino)-1H-isoindol-4-yl 4-(2-pyridinyl)-1-piperazinyl-carbamate;
2,3-dihydro-4-fluoro-2-(-4-pyridinylamino)-1H-isoindol-5-ol hydrobromide;
2-(4-pyridinylamino)-1,2,3,4-tetrahydro-isoquinolin-7-ol;
8-chloro-2-(4-pyridinylamino)-1,2,3,4-tetrahydro-isoquinolin-5-ol hydrobromide;
(5-methoxy-3,4-dihydro-1H-isoquinolin-2-yl)-4-pyridinylamine dihydrochloride;
(7-benzyloxy-5-bromo-8-methoxy-3,4-dihydro-1H-isoquinolin-2-yl)-4-pyridinylamine hydrochloride;
2,3-dihydro-4-chloro-7-methoxy-N-(4-pyridinyl)-1H-isoindol-2-amine;
2,3-dihydro-2-(4-pyridinylamino)-1H-isoindol-4-yl N-benzyl-N-methylcarbamate hydrochloride hemihydrate;
(3,4-dihydro-8-benzyloxy-5-bromo-7-methoxy-1H-isoquinolin-2-yl)-4-pyridinylamine fumarate;
7-methoxy-2-(4-pyridinylamino)-1,2,3,4-tetrahydroisoquinolin-8-ol hydrobromide;
7-methoxy-2-(4-pyridinylamino)-1,2,3,4-tetrahydroisoquinolin-8-yl dimethyl carbamate fumarate;
2,3-dihydro-2-(4-pyridinylamino)-1H-isoindol-4-yl diethylcarbamate hydrochloride;
2,3-dihydro-4-fluoro-2-(4-pyridinylamino)-1H-isoindol-5-yl dimethylcarbamate hydrochloride;
2,3-dihydro-4-chloro-2-(4-pyridinylamino)-1H-isoindol-7-ol dihydrobromide;
2,3-dihydro-4-fluoro-2-(4-pyridinylamino)-1H-isoindol-5-yl 1,2,3,4-tetrahydroisoquinolin-2-ylcarbamate hydrochloride;
2-(4-pyridinylamino)-1,2,3,4-tetrahydro-isoquinolin-5-ol hydrobromide monohydrate;
3,4-dihydro-1H-isoquinolin-2-carboxylic acid-7-methoxy-2-(4-pyridinylamino)-2,3,4,5-tetrahydro-1H-benzo[c]azepin-8-yl ester hydrochloride;
2,3-dihydro-4-chloro-2-(4-pyridylamino)-1H-isoindol-7-yl dimethyl carbamate hydrochloride; and
2,3-dihydro-2-(4-pyridinylamino)-1H-isoindol-4-yl 4-(2-pyridinyl)-1-piperazinyl-carbamate ¼ hydrate.

* * * * *